United States Patent
Vale et al.

(10) Patent No.: US 11,395,667 B2
(45) Date of Patent: Jul. 26, 2022

(54) CLOT RETRIEVAL SYSTEM FOR REMOVING OCCLUSIVE CLOT FROM A BLOOD VESSEL

(71) Applicant: NEURAVI LIMITED, Galway (IE)

(72) Inventors: David Vale, County Galway (IE); Brendan Casey, Galway (IE); Brian Fahy, County Galway (IE); Kevin McArdle, County Galway (IE); Eamon Brady, County Galway (IE); Jill Amstutz, Menlo Park, CA (US); Maeve Holian, County Galway (IE); Daniel King, County Galway (IE); Michael Gilvarry, County Galway (IE)

(73) Assignee: NEURAVI LIMITED, Galway (IE)

( * ) Notice: Subject to any disclaimer, the term of this patent is extended or adjusted under 35 U.S.C. 154(b) by 134 days.

(21) Appl. No.: 16/326,030

(22) PCT Filed: Aug. 3, 2017

(86) PCT No.: PCT/EP2017/069668
§ 371 (c)(1),
(2) Date: Feb. 15, 2019

(87) PCT Pub. No.: WO2018/033401
PCT Pub. Date: Feb. 22, 2018

(65) Prior Publication Data
US 2019/0167287 A1    Jun. 6, 2019

Related U.S. Application Data

(60) Provisional application No. 62/376,264, filed on Aug. 17, 2016.

(51) Int. Cl.
*A61B 17/22* (2006.01)
*A61M 25/10* (2013.01)
(Continued)

(52) U.S. Cl.
CPC ........ *A61B 17/22032* (2013.01); *A61B 17/22* (2013.01); *A61B 17/221* (2013.01);
(Continued)

(58) Field of Classification Search
CPC . A61B 17/22032; A61B 17/22; A61B 17/221; A61B 2017/22054;
(Continued)

(56) References Cited

U.S. PATENT DOCUMENTS 4,243,040 A    1/1981 Beecher
4,324,262 A    4/1982 Hall
(Continued)

FOREIGN PATENT DOCUMENTS

CN    1658920 A    8/2005
CN    1972728 A    5/2007
(Continued)

OTHER PUBLICATIONS

US 6,348,062 B1, 02/2002, Hopkins (withdrawn)
(Continued)

*Primary Examiner* — Kathleen S Holwerda
*Assistant Examiner* — Uyen N Vo
(74) *Attorney, Agent, or Firm* — Troutman Pepper Hamilton Sanders LLP

(57) ABSTRACT

A clot capture catheter comprises an elongate tubular shaft having a proximal end, a distal end and an inflatable expansile member at the distal end. The expansile member is inflatable from a collapsed delivery configuration to an expanded configuration. In the expanded configuration, the expansile member extends to define a funnel shape having an enlarged distal clot entry mouth at the distal-most end of the catheter. In the expanded configuration, the expansile
(Continued)

member may extend distally beyond the distalmost tip of the shaft. The expansile member may be integral with the distal tip of the catheter shaft.

14 Claims, 14 Drawing Sheets

(51) Int. Cl.
*A61B 17/221* (2006.01)
*A61F 2/95* (2013.01)

(52) U.S. Cl.
CPC ............ *A61F 2/95* (2013.01); *A61M 25/1002* (2013.01); *A61M 25/1011* (2013.01); *A61B 2017/22054* (2013.01); *A61B 2017/22062* (2013.01); *A61B 2017/22067* (2013.01); *A61B 2017/22069* (2013.01); *A61B 2017/22079* (2013.01); *A61B 2217/005* (2013.01); *A61F 2002/9528* (2013.01); *A61M 25/1018* (2013.01); *A61M 25/1034* (2013.01); *A61M 2025/109* (2013.01); *A61M 2025/1013* (2013.01); *A61M 2025/1047* (2013.01); *A61M 2025/1059* (2013.01); *A61M 2025/1065* (2013.01); *A61M 2025/1079* (2013.01); *A61M 2025/1084* (2013.01); *A61M 2025/1093* (2013.01); *A61M 2205/0216* (2013.01)

(58) Field of Classification Search
CPC  A61B 2017/22062; A61B 2017/22067; A61B 2017/22069; A61B 2017/22079; A61F 2/95; A61F 2002/9528; A61M 25/1002; A61M 25/1011; A61M 2025/1004; A61M 2025/1013; A61M 2025/1047; A61M 2025/1059; A61M 2025/1065; A61M 2025/1079; A61M 2025/1084; A61M 2025/109; A61M 2025/1093
See application file for complete search history.

(56) References Cited

U.S. PATENT DOCUMENTS

| | | | |
|---|---|---|---|
| 4,351,342 A * | 9/1982 | Wiita | A61M 25/1002 604/101.05 |
| 4,575,371 A | 3/1986 | Nordqvist et al. | |
| 4,719,924 A | 1/1988 | Crittenden et al. | |
| 4,738,666 A | 4/1988 | Fuqua | |
| 4,767,404 A | 8/1988 | Renton | |
| 4,793,348 A | 12/1988 | Palmaz | |
| 4,873,978 A | 10/1989 | Ginsburg | |
| 5,011,488 A | 4/1991 | Ginsburg | |
| 5,092,839 A | 3/1992 | Kipperman | |
| 5,102,415 A | 4/1992 | Guenther et al. | |
| 5,122,136 A | 6/1992 | Guglielmi et al. | |
| 5,123,840 A | 6/1992 | Nates | |
| 5,171,233 A | 12/1992 | Amplatz | |
| 5,234,437 A | 8/1993 | Sepetka | |
| 5,256,144 A | 10/1993 | Kraus et al. | |
| 5,372,124 A | 12/1994 | Takayama et al. | |
| 5,385,562 A | 1/1995 | Adams | |
| 5,387,219 A | 2/1995 | Rappe | |
| 5,387,226 A | 2/1995 | Miraki | |
| 5,396,902 A | 3/1995 | Brennen et al. | |
| 5,449,372 A | 9/1995 | Schmaltz | |
| 5,520,651 A | 5/1996 | Sutcu | |
| 5,538,512 A | 7/1996 | Zenzon et al. | |
| 5,549,626 A | 8/1996 | Miller et al. | |
| 5,558,652 A | 9/1996 | Henke | |
| 5,609,627 A | 3/1997 | Goicoechea et al. | |
| 5,624,461 A | 4/1997 | Mariant | |
| 5,639,277 A | 6/1997 | Mariant | |
| 5,645,558 A | 7/1997 | Horton | |
| 5,658,296 A | 8/1997 | Bates | |
| 5,662,671 A | 9/1997 | Barbut | |
| 5,695,519 A | 12/1997 | Summer et al. | |
| 5,709,704 A | 1/1998 | Nott et al. | |
| 5,713,853 A | 2/1998 | Clark | |
| 5,728,078 A | 3/1998 | Powers, Jr. | |
| 5,769,871 A | 6/1998 | Mers Kelly | |
| 5,779,716 A | 7/1998 | Cano | |
| 5,810,874 A | 9/1998 | Lefebvre | |
| 5,814,064 A | 9/1998 | Danniel et al. | |
| 5,827,304 A | 10/1998 | Hart | |
| 5,855,598 A | 1/1999 | Pinchuk | |
| 5,893,869 A | 4/1999 | Barnhart et al. | |
| 5,895,398 A | 4/1999 | Wensel | |
| 5,897,567 A | 4/1999 | Ressemann | |
| 5,904,698 A | 5/1999 | Thomas et al. | |
| 5,911,725 A | 6/1999 | Boury | |
| 5,935,139 A | 8/1999 | Bates | |
| 5,938,645 A | 8/1999 | Gordon | |
| 5,947,995 A | 9/1999 | Samuels | |
| 5,968,057 A | 10/1999 | Taheri | |
| 5,971,938 A | 10/1999 | Hart et al. | |
| 5,997,939 A | 12/1999 | Moechnig et al. | |
| 6,063,113 A | 5/2000 | Kavteladze | |
| 6,066,149 A | 5/2000 | Samson et al. | |
| 6,066,158 A | 5/2000 | Engelson | |
| 6,093,196 A | 7/2000 | Okada | |
| 6,093,199 A | 7/2000 | Brown et al. | |
| 6,096,053 A | 8/2000 | Bates | |
| 6,099,534 A | 8/2000 | Bates | |
| 6,102,932 A | 8/2000 | Kurz | |
| 6,106,548 A | 8/2000 | Roubin et al. | |
| 6,129,739 A | 10/2000 | Khosravi | |
| 6,146,396 A | 11/2000 | Kónya et al. | |
| 6,146,404 A | 11/2000 | Kim | |
| 6,165,194 A | 12/2000 | Denardo | |
| 6,165,199 A | 12/2000 | Barbut | |
| 6,168,604 B1 | 1/2001 | Cano | |
| 6,168,622 B1 | 1/2001 | Mazzocchi | |
| 6,174,318 B1 | 1/2001 | Bates et al. | |
| 6,179,861 B1 | 1/2001 | Khosravi | |
| 6,203,561 B1 | 3/2001 | Ramee | |
| 6,214,026 B1 | 4/2001 | Lepak | |
| 6,221,006 B1 | 4/2001 | Dubrul | |
| 6,238,412 B1 | 5/2001 | Dubrul | |
| 6,245,087 B1 | 6/2001 | Addis | |
| 6,251,122 B1 | 6/2001 | Tsukernik | |
| 6,254,571 B1 | 7/2001 | Hart | |
| 6,264,663 B1 | 7/2001 | Cano | |
| 6,306,163 B1 | 10/2001 | Fitz | |
| 6,309,379 B1 | 10/2001 | Willard | |
| 6,312,444 B1 | 11/2001 | Barbut | |
| 6,315,778 B1 | 11/2001 | Gambale et al. | |
| 6,325,819 B1 | 12/2001 | Pavcnik et al. | |
| 6,334,864 B1 | 1/2002 | Amplatz et al. | |
| 6,336,934 B1 | 1/2002 | Gilson et al. | |
| 6,348,056 B1 | 2/2002 | Bates | |
| 6,350,271 B1 | 2/2002 | Kurz et al. | |
| 6,361,545 B1 | 3/2002 | Macoviak | |
| 6,375,668 B1 | 4/2002 | Gifford et al. | |
| 6,383,205 B1 | 5/2002 | Samson et al. | |
| 6,383,206 B1 | 5/2002 | Gillick | |
| 6,391,037 B1 | 5/2002 | Greenhalgh | |
| 6,402,771 B1 | 6/2002 | Palmer | |
| 6,409,683 B1 | 6/2002 | Fonseca et al. | |
| 6,416,541 B2 | 7/2002 | Denardo | |
| 6,425,909 B1 | 7/2002 | Dieck et al. | |
| 6,432,122 B1 | 8/2002 | Gilson et al. | |
| 6,436,112 B2 | 8/2002 | Wensel | |
| 6,458,139 B1 | 10/2002 | Palmer | |
| 6,346,116 B1 | 11/2002 | Brooks et al. | |
| 6,485,497 B2 | 11/2002 | Wensel | |
| 6,485,501 B1 | 11/2002 | Green | |
| 6,485,502 B2 | 11/2002 | Don Michael | |
| 6,511,492 B1 | 1/2003 | Rosenbluth | |
| 6,517,551 B1 | 2/2003 | Driskill | |
| 6,520,934 B1 * | 2/2003 | Lee | A61M 25/0108 604/103.1 |
| 6,520,951 B1 | 2/2003 | Carrillo, Jr. | |

(56) References Cited

U.S. PATENT DOCUMENTS

| | | |
|---|---|---|
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hanoock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |

(56) References Cited

U.S. PATENT DOCUMENTS

| | | |
|---|---|---|
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,716,915 B2 | 7/2020 | Ogle et al. |
| 10,610,668 B2 | 8/2020 | Burkholz et al. |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1* | 11/2001 | Parodi .............. A61B 17/12022 604/104 |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1* | 1/2003 | Vo ..................... A61M 25/1002 604/103.07 |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbu |
| 2003/0176884 A1 | 9/2003 | Berrada et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153118 A1 | 8/2004 | Clubb |
| 2004/0193107 A1 | 9/2004 | Pierpont et al. |
| 2004/0199202 A1* | 10/2004 | Dubrul .................. A61B 90/39 606/200 |
| 2004/0260333 A1 | 12/2004 | Dubrul et al. |
| 2005/0015047 A1* | 1/2005 | Shah .................. A61M 25/1011 604/101.02 |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |

(56) References Cited

U.S. PATENT DOCUMENTS

| | | |
|---|---|---|
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1* | 12/2009 | Tilson ............... A61B 17/8816 606/94 |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0030186 A1 | 2/2010 | Stivland |
| 2010/0030256 A1 | 2/2010 | Dubrul et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |

(56) References Cited

U.S. PATENT DOCUMENTS

| | | |
|---|---|---|
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257362 A1 | 9/2014 | Eldenschink |
| 2014/0276922 A1 | 9/2014 | McLain et al. |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |
| 2017/0296325 A1 | 10/2017 | Marrocco et al. |

(56) References Cited

U.S. PATENT DOCUMENTS

| | | |
|---|---|---|
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0042623 A1 | 2/2018 | Batiste |
| 2018/0193591 A1 | 7/2018 | Jaroch et al. |
| 2018/0235743 A1 | 8/2018 | Farago et al. |
| 2019/0021759 A1 | 1/2019 | Krolik et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0255290 A1 | 8/2019 | Snyder et al. |
| 2019/0365411 A1 | 12/2019 | Avneri et al. |

FOREIGN PATENT DOCUMENTS

| | | |
|---|---|---|
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| EP | 2301450 A1 | 3/2011 |
| EP | 2628455 A1 | 8/2013 |
| EP | 3302312 A1 | 4/2018 |
| EP | 3 420 978 A1 | 1/2019 |
| GB | 2498349 A | 7/2013 |
| JP | 9-19438 A | 1/1997 |
| WO | WO 93/04722 A1 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |
| WO | 99/56801 A2 | 11/1999 |
| WO | 99/60933 A1 | 12/1999 |
| WO | 01/21077 A1 | 3/2001 |
| WO | 02/02162 A2 | 1/2002 |
| WO | 02/11627 A2 | 2/2002 |
| WO | 02/43616 A2 | 6/2002 |
| WO | 02/070061 A1 | 9/2002 |
| WO | 02/094111 A2 | 11/2002 |
| WO | 03/002006 A1 | 1/2003 |
| WO | 03/018085 A2 | 3/2003 |
| WO | 03/030751 A1 | 4/2003 |
| WO | 03/051448 A2 | 6/2003 |
| WO | 2004/028571 A1 | 4/2004 |
| WO | 2004/056275 A1 | 7/2004 |
| WO | 2005/000130 A1 | 1/2005 |
| WO | 2005/027779 A2 | 3/2005 |
| WO | WO 2005/027751 A1 | 3/2005 |
| WO | 2006/021407 A2 | 3/2006 |
| WO | 2006/031410 A2 | 3/2006 |
| WO | 2006/107641 A2 | 10/2006 |
| WO | 2006/135823 A2 | 12/2006 |
| WO | 2007/054307 A2 | 5/2007 |
| WO | 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | WO 2009/019664 A1 | 2/2009 |
| WO | 2009/031338 A1 | 3/2009 |
| WO | 2009/076482 A1 | 6/2009 |
| WO | 2009/086482 A2 | 7/2009 |
| WO | 2009/105710 A1 | 8/2009 |
| WO | WO 2009/103125 A1 | 8/2009 |
| WO | 2010/010545 A1 | 1/2010 |
| WO | 2010/046897 A1 | 4/2010 |
| WO | 2010/075565 A1 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/110619 A1 | 8/2012 |
| WO | 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | 2015/061365 A1 | 4/2015 |
| WO | 2015/134625 A1 | 9/2015 |
| WO | 2015/179324 A2 | 11/2015 |
| WO | WO 2015/179377 A1 | 11/2015 |
| WO | 2015/189354 A1 | 12/2015 |
| WO | 2016/010995 A1 | 1/2016 |
| WO | WO 2017/004234 A1 | 1/2017 |
| WO | 2018/193603 A1 | 10/2018 |
| WO | WO 2018/178979 A1 | 10/2018 |
| WO | WO 2019/064306 A1 | 4/2019 |
| WO | WO 2019/079296 A1 | 4/2019 |
| WO | WO 2020/139979 A1 | 7/2020 |

OTHER PUBLICATIONS

International Search Report and Written Opinion issued for Application No. PCT/EP2017/069668 dated Nov. 27, 2017.
International Search Report and Written Opinion issued for Application No. PCT/EP2017/0696688 dated Nov. 27, 2017.
International Search Report of PCT/IE2011/000057, dated Feb. 3, 2012 (5 pages).
International Search Report of PCT/IE2012/000011, dated Oct. 10, 2012 (3 pages).
Office Action issued in U.S. Appl. No. 14/737,249 dated Apr. 10, 2018.
Office Action issued in U.S. Appl. No. 15/158,384 dated Jul. 20, 2018.
Partial European Search Report issued in Application 17204015.6 dated May 17, 2018.
U.S. Office Action issued in corresponding U.S. Appl. No. 15/158,384 dated Jun. 12, 2019.
Written Opinion and International Search Report, dated Jul. 27, 2011, from international Application No. PCT/IE2011/000026 (8 pages).
Extended European Search Report issued in corresponding European Patent Application No. 20 19 5533 dated Feb. 8, 2021.
European Search Report issued in corresponding EP Appln. No. 20 19 7446 dated Jan. 19, 2021.
Struffert, T., et al. "Intravenous flat detector CT angiography for non-invasive visualisation of intracranial flow diverter: technical feasibility" Eur Radiol 21:1797-1801 (2011).

(56) References Cited

OTHER PUBLICATIONS

Extended European Search Report dated Jul. 28, 2021 issued in European Patent Application No. 20 21 0069.
Extended European Search Report dated Aug. 5, 2021 issued in European Patent Application No. 21 16 7037.

\* cited by examiner

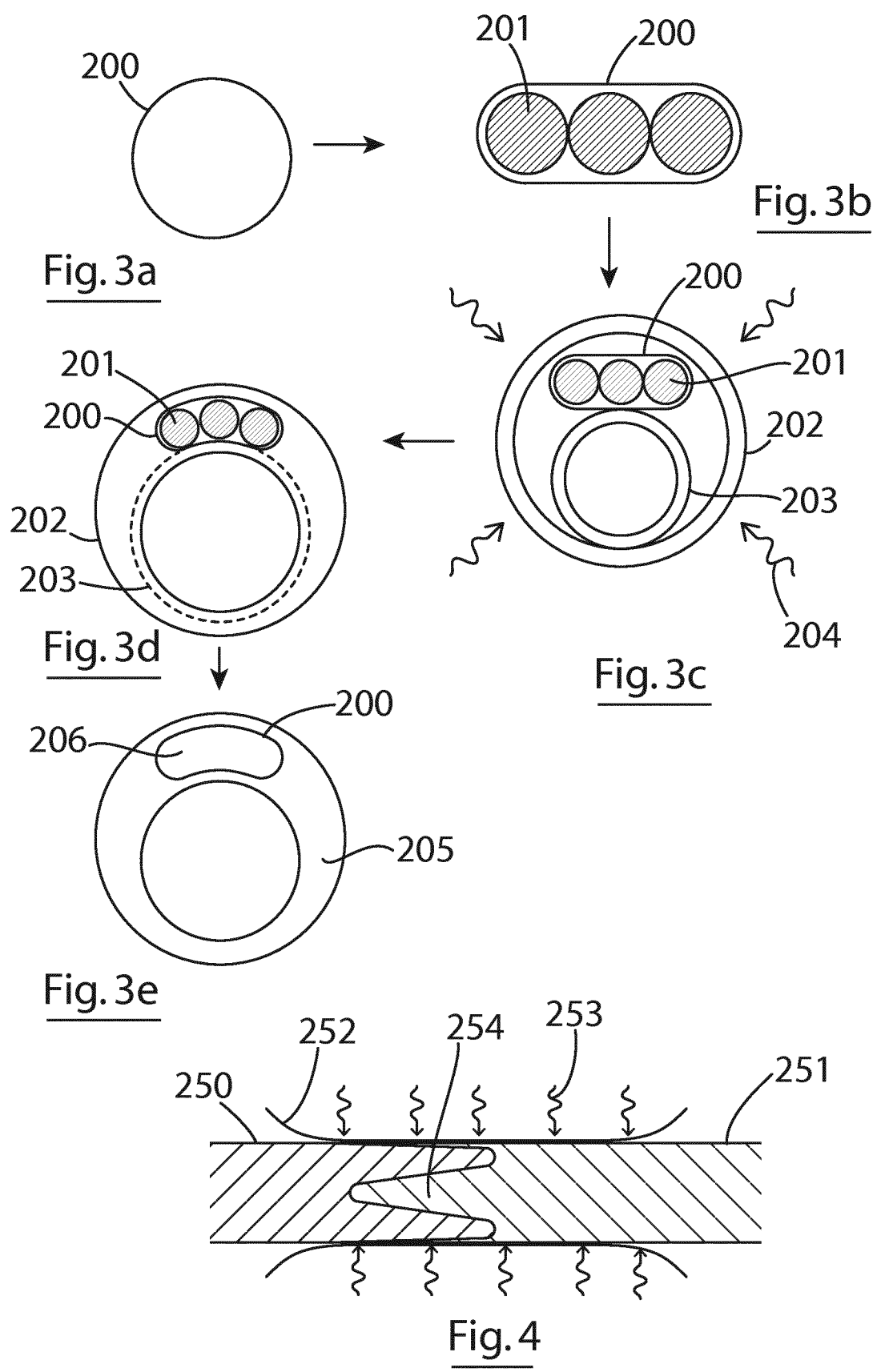

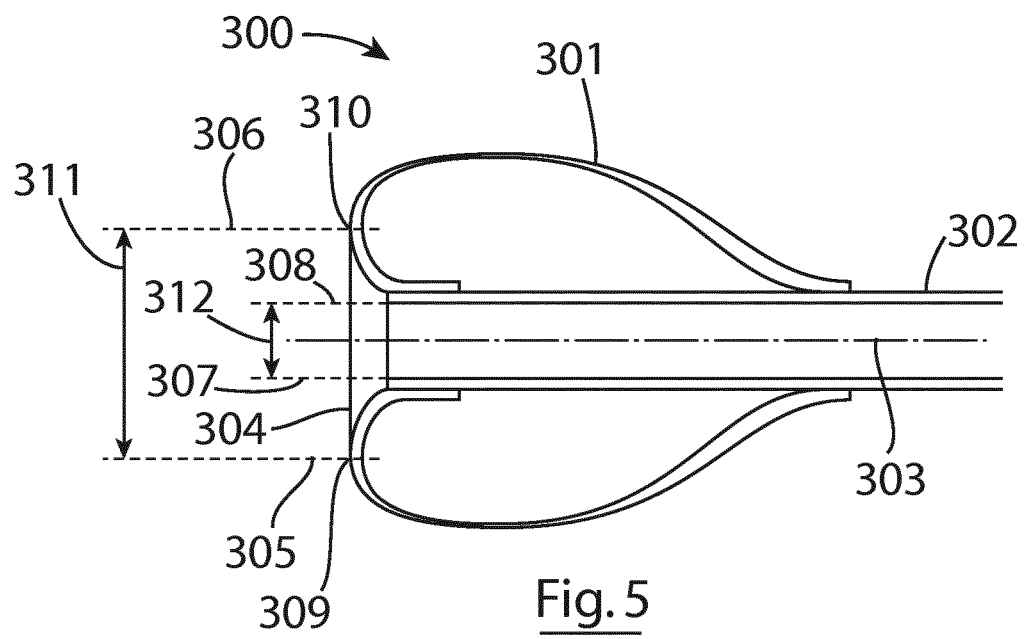
Fig. 5
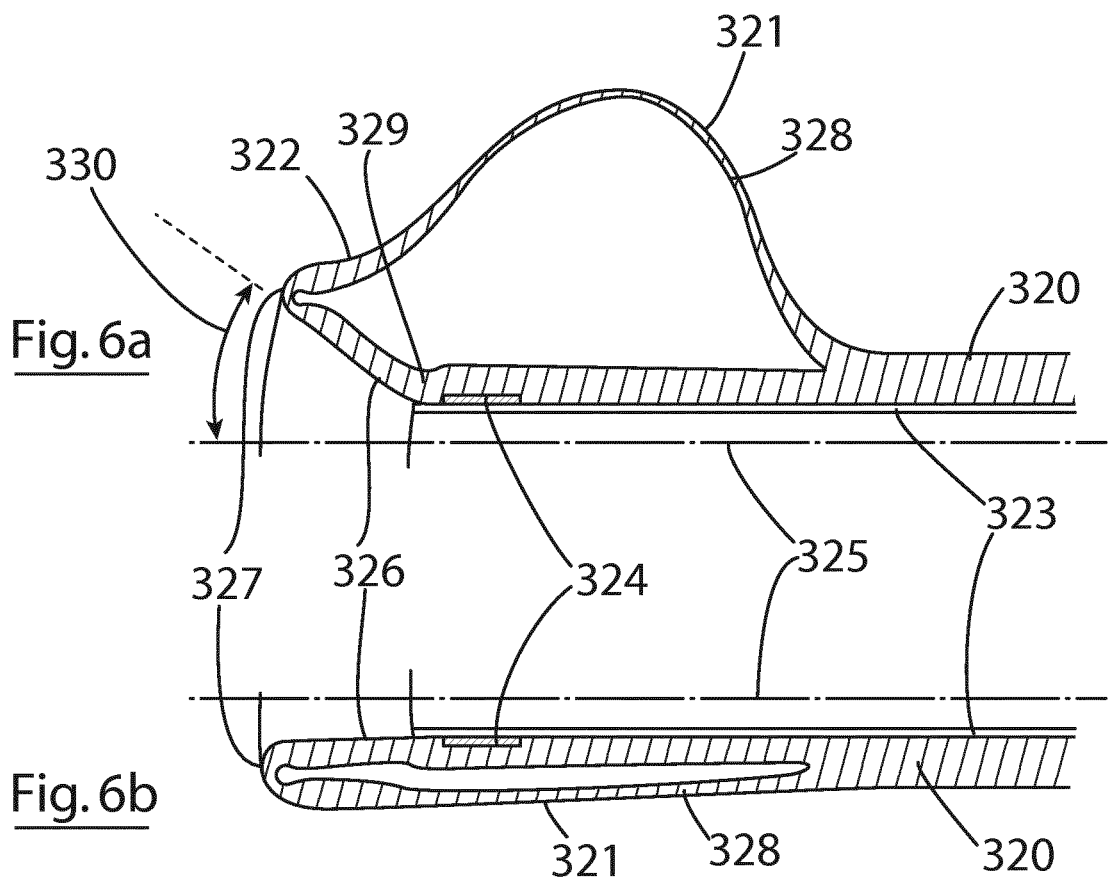
Fig. 6a
Fig. 6b

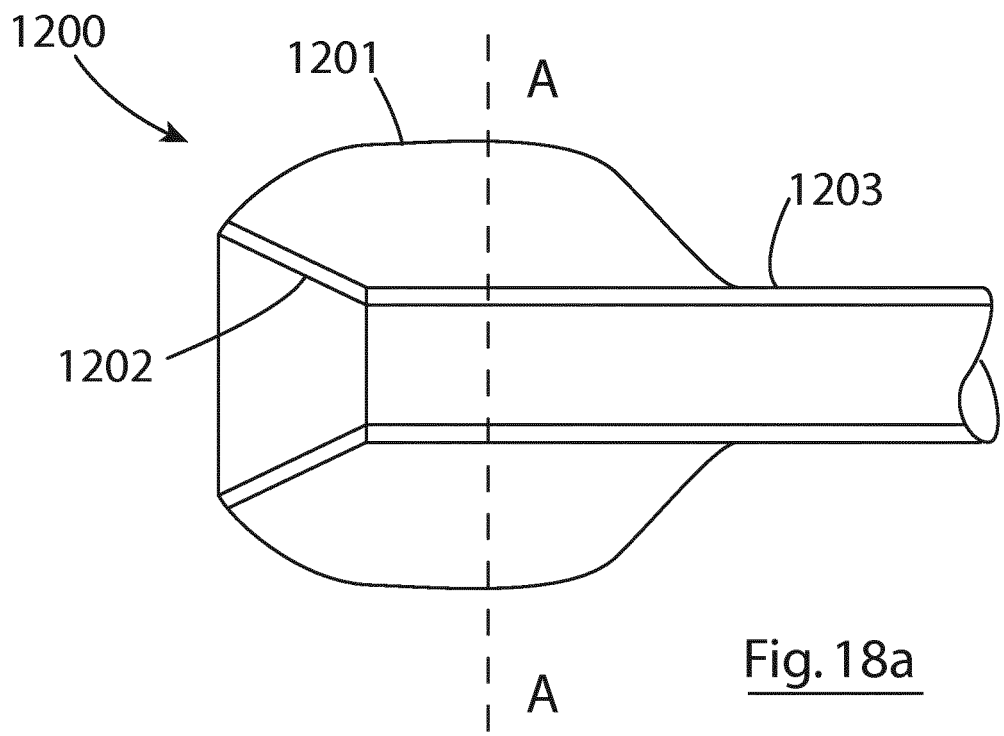
Fig. 18a
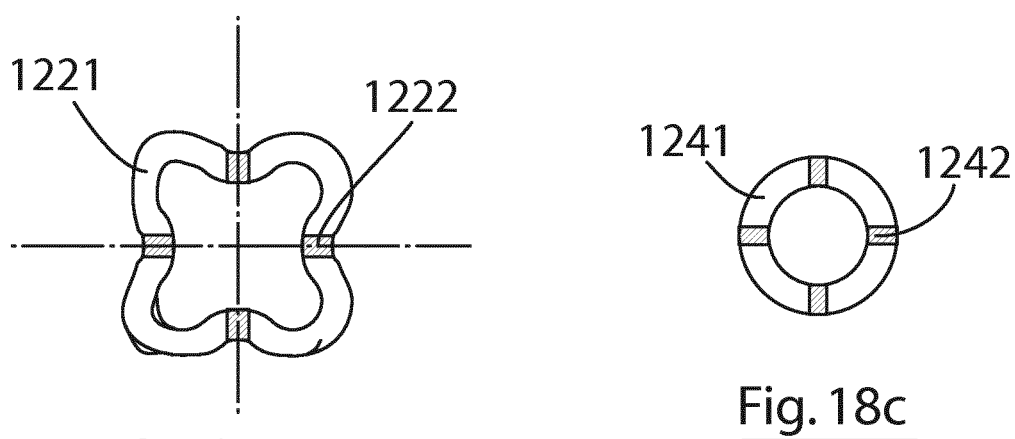
Section A-A
Fig. 18b
Fig. 18c
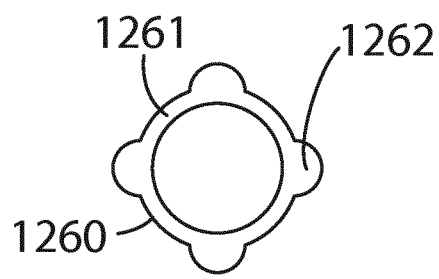
Fig. 18d

CLOT RETRIEVAL SYSTEM FOR REMOVING OCCLUSIVE CLOT FROM A BLOOD VESSEL

CROSS-REFERENCE TO RELATED APPLICATIONS

This application is a United States national stage entry of an International Application No. PCT/EP2017/069668 filed Aug. 3, 2017, which claims priority to European Patent Application No. 16186028.3 filed Aug. 26, 2016, and U.S. Provisional Application No. 62/376,264 filed Aug. 17, 2016. The contents of these applications are incorporated herein by reference in their entirety as if set forth verbatim.

FIELD OF THE INVENTION

This invention relates to devices intended for use in procedures involving removing acute blockages from blood vessels. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited for use in cases involving the removal of clot from cerebral arteries in patients suffering acute ischemic stroke (AIS), from coronary native or graft vessels in patients suffering from myocardial infarction (MI), and from pulmonary arteries in patients suffering from pulmonary embolism (PE) and from other peripheral arterial and venous vessels in which clot is causing an occlusion.

BACKGROUND INFORMATION

Recent clinical studies have shown that mechanical thrombectomy is a very effective method of restoring blood flow to the ischemic tissue of patients who have recently suffered an acute ischemic stroke. This procedure typically involves advancing a thrombectomy device (which may be a stent-retriever and/or an aspiration catheter) to the occlusive clot, engaging with the clot and retracting the clot into the safety of a local aspiration catheter or a more proximally placed guide or sheath. In the latter case a balloon guide catheter is often employed, as with such a catheter the balloon can be inflated to restrict flow past the catheter, which makes it easier to safely retrieve the captured clot into the catheter mouth. Aspiration through the balloon guide catheter is typically used to reverse flow in the distal vasculature and assist the passage of the captured clot into the catheter mouth.

However, despite the benefits provided by balloon guides, there are significant limitations to currently available devices:

One of these limitations is due to the location of the balloon on the catheter. Conventional balloon guide catheters have a "dead space" distal to the balloon because of the manner in which the distal neck of the balloon is attached to the catheter shaft and because of the presence of a distal catheter tip. This dead space is a region from which clot cannot easily be aspirated or sucked, and thus if clot fragments become lodged in this region they may escape distally upon deflation of the balloon (which must be done prior to removal of the catheter from the patient), potentially causing occlusion of a blood vessel and serious patient harm.

A second limitation of conventional balloon guide catheters is the level of shear stress induced in the clot as it withdrawn into the catheter. This stress is influenced by a number of factors, including the relative size of the clot and catheter lumen and the coefficient of friction of the clot relative to the catheter. The clot entering the catheter must abruptly change in shape to conform to the inner diameter of the catheter in order to enter the catheter. This abrupt change can create a high shear stress at the interface between clot and catheter tip, which can result in shearing or tearing of the clot, releasing clot fragments which may then hang up in the previously mentioned dead space, or causing large portions or the entirety of the clot to be dislodged from the stent-retriever or aspiration catheter which has retracted it to the balloon guide catheter. If these clot portions or fragments are not then aspirated fully into the balloon guide catheter they may travel distally and cause injury or death.

STATEMENTS OF THE INVENTION

This invention solves the previously described problems of clot shear and clot fragments lodging in the "dead space" at the distal tip of a balloon guide catheter. The subject of this invention is a catheter configured for use in a mechanical thrombectomy procedure comprising an elongate tubular shaft with an expandable distal tip portion.

The elongate shaft comprises a first inner lumen through which other catheters or components may be passed and through which clot may be aspirated, and a second inner lumen within the wall of the shaft running from the proximal hub of the catheter to an inflatable member at the distal end of the shaft. This second inner lumen may be circular in cross section, or may be oblong, and may comprise multiple lumens.

One embodiment of the expandable distal tip portion comprises a funnel shaped balloon and has a collapsed and an expanded state. In the collapsed state the balloon is deflated and may be folded and/or pleated in order to minimize its profile for advancement through an introducer sheath and through the vasculature of the patient. In the expanded state the balloon is inflated. Inflation of the balloon serves a number of purposes:

1) The balloon can be inflated to a diameter that brings it into contact with the vessel wall, thus partially or completely preventing blood flow past the balloon. This in turn may help to reduce the likelihood of some or all of the clot being retrieved into the catheter during a thrombectomy procedure. This also facilitates effective aspiration through the catheter, ensuring that this aspiration creates reverse flow in the distal vessel.
2) Inflation of the balloon can help to stabilize the catheter within the vessel, preventing unintended catheter movement and consequent vessel trauma.
3) Inflation of the balloon of this invention also changes the shape of the catheter tip, optimizing the geometry of the interface between the catheter tip and any material or devices being withdrawn into it. In particular this shape change reduces the shear forces exerted on thrombus material as it is withdrawn into the catheter, and minimizes or eliminates any "dead space" or pocket in which thrombus might be caught.

In one embodiment of this invention the funnel shaped balloon is integral to the distal catheter tip portion and is formed from a length of polymer tubing which is inverted so that the distal junction between the balloon and catheter sits under (and within) the balloon itself.

The balloon wall thickness may be profiled/tapered in order to force the balloon to preferentially expand more in certain areas than in others, thus enabling a funnel shaped profile to be attained upon inflation. In one embodiment the wall thickness of the proximal and distal portions of the balloon is greater than that of the middle section. In another embodiment the wall thickness of the proximal portion of the balloon is greater than that of the middle and distal sections.

In another embodiment a proximal portion of the balloon is reinforced in order to limit its expansion when inflated, thus causing preferential expansion of the distal portion of the balloon and creating a bulbous funnel shape at the distal end. This reinforcement may be in the form of ribs, which may run axially or radially along the balloon, and/or may be formed from the same or a different material to the balloon itself.

The inverted balloon may be positioned such that it overhangs the catheter tip, in which case the balloon material is not under any axial tension in the unexpanded state, unlike most conventional compliant balloons. This lack of axial tension combined with a degree of overhang (ideally greater than 0.5 mm but less than 3.5 mm) is key to ensuring the balloon can inflate to a funnel-like shape.

The balloon may be pre-formed into a funnel-like shape prior to assembly onto the catheter shaft, in which case it may be beneficial to also provide it with pleats or preferential fold lines in order to facilitate efficient wrap down to a low profile.

In one series of embodiments multiple balloons are employed on the catheter shaft. This has the benefit of allowing individual balloon properties to be tailored for specific tasks. For example a low pressure, compliant, balloon may be designed to seal against the vessel wall to help create flow arrest, while another balloon may be designed to adopt a funnel-like shape at the distal catheter tip to minimize shear forces on the clot and facilitate easy entry of large and/or firm clots into the catheter mouth. In some cases a higher pressure, less compliant, balloon may be employed to help keep the catheter tip from lying too close to the vessel wall and impeding clot retrieval.

The materials used in the construction of this catheter must be carefully selected. For high pressure balloons relatively high modulus materials such as PET or Polyamide make good choices, but for certain inflatable portions of the catheters of this invention a much softer more compliant material is desired. This preferably comprises an amorphous elastomeric polymer, so that it can be stretched/strained under inflation pressure to a diameter at least twice and as much as 5 times its uninflated diameter and recover most or all of its unexpanded shape upon deflation. This requires the material to withstand an elastic strain of at least 200% and ideally 500% or more with minimal levels of plastic deformation. Recoverable strains of such a high level are greatly facilitated by crosslinking of the polymer chains, and hence thermoset materials such as silicone rubbers may be a good choice for a compliant balloon. However silicone is not an easy material to join to a second material as it cannot easily be melted and made miscible with another material to form a strong and low profile weld joint for example. For this reason polyurethane elastomers are a preferred material for the balloon of this invention. In particular thermoplastic polyurethane elastomers would make an ideal material as this can be melted as part of a welding or joining process, or can be solvent bonded or adhesively bonded. In addition such polyurethanes can be joined to compatible families of materials in order to create a greater stiffness gradient along the length of the catheter than would be possible if limited to polyurethanes alone. For example, a very soft polyurethane can be used for the balloon and very distal section of the catheter; one or more Pebax (polyether block amide copolymer) materials may be used for a mid-section of the catheter; and polyamide material(s) may be used for the proximal section of the catheter shaft. This series of materials offers increasingly higher durometers and Young's modulus (or stiffness), so that a very flexible distal shaft region can be smoothly transitioned to a much stiffer proximal shaft region. The Polyether block amide material has the advantage of being joinable to both the Polyurethane and the Polyamide, even though the Polyurethane and the Polyamide are not so easily joined to one another.

In one aspect the invention provides a clot capture catheter comprising an elongate tubular shaft having a proximal end, a distal end and an inflatable expansile member at the distal end, the expansile member being inflatable from a collapsed delivery configuration to an expanded configuration, wherein, in the expanded configuration, the expansile member extends to at least the distalmost tip of the shaft and extends radially outwardly from the shaft at the distalmost tip of the shaft to define a mouth.

In one aspect the invention provided a clot capture catheter comprising an elongate tubular shaft having a proximal end, a distal end and an inflatable expansile member at the distal end, the expansile member being inflatable from a collapsed delivery configuration to an expanded configuration, wherein, in the expanded configuration, the expansile member extends radially outwardly at the distalmost tip of the catheter to define a funnel shaped profile having an enlarged distal clot entry mouth.

In one embodiment, in the expanded configuration, the diameter of the distalmost portion of the catheter defined by the expansile member is larger than the diameter of the generally cylindrical inner lumen of the distal region of the catheter.

In one case, in the expanded configuration, the expansile member extends distally beyond the distalmost tip of the shaft.

In one embodiment the expansile member comprises a balloon. The balloon, in the expanded configuration, may be of funnel shape having an enlarged distal entry mouth and a narrower proximal end.

In one case the balloon is integral to the distal tip of the catheter shaft.

The expansile member may be formed from a polymeric tube which is inverted so that a distal junction between the balloon and the catheter shaft is located within the balloon.

In one embodiment the balloon comprises regions which have different properties to one another.

The balloon may comprise a proximal region, a distal region and a median region between the proximal and distal regions and wherein, in the expanded configuration, the distal region expands to a greater extent than the proximal region.

In one case at least one region has a different wall thickness than at least one other region.

In one case the wall thickness of the proximal and distal regions is greater than the wall thickness of the median region.

In one embodiment the wall thickness of the proximal region is greater than the wall thickness of the median region and the distal region.

In one case the expansile member comprises a proximal neck and a distal neck, the proximal neck having a first thickness, and being connected to the catheter shaft proximal of the distal end of the catheter, a proximal portion of the expansile member comprising a second thickness, a distal portion of the expansile member comprising a third thickness, and the distal neck, which is inverted and joined to the distal end of the catheter shaft, comprising a fourth thickness.

In one embodiment a mid-portion of the expansile member comprises a variable thickness which tapers from the second thickness to the third thickness.

In one case the first thickness is greater than the second thickness, and the second thickness is greater than the third thickness.

In one embodiment the fourth thickness is greater than the third thickness.

In one case the fourth thickness is greater than the first thickness.

In one embodiment the first thickness is approximately the same as the second thickness in the deflated state, but is greater than the second thickness in the inflated state.

In one case a band is provided between the proximal and distal regions of the expansile member, the band having a greater wall thickness than the wall thickness of the proximal and/or distal region, to create a relatively non-expansile region such that the expansile member preferentially inflates proximal and distal of the band to provide a funnel shape profile.

In one case at least one of the regions is reinforced to limit the expansion of that region.

In one embodiment the proximal region comprises a reinforcement.

In one case the reinforcement comprises ribs.

The ribs may extend axially and/or radially along at least a portion of the proximal region.

In one embodiment the ribs are of the same or a different material than that of the balloon.

In one case the expansile member in the collapsed configuration extends beyond the distal tip of the catheter shaft.

The expansile member may extend beyond the distal tip of the catheter shaft for a distance of from 0.5 mm to 3.5 mm.

In one embodiment the catheter shaft comprises a main inner lumen, and an inflation lumen for inflating the expansile member.

The inflation lumen may extend within the wall of catheter shaft.

In one case the inflation lumen and the catheter lumen are eccentric.

In a further case the inflation lumen and the catheter lumen are concentric.

In one case the inflatable expansile member comprises an amorphous elastomeric polymer.

The elastomeric polymer may be a thermoplastic polyurethane elastomer.

In one embodiment a portion of the shaft of the catheter comprises the inflatable expansile member.

In one case a distal region of the catheter shaft comprises an amorphous elastomeric polymer.

In one embodiment the amorphous elastomeric polymer of the distal region of the catheter is a thermoplastic polyurethane elastomer.

In one case a distal portion of the shaft comprises a first amorphous elastomeric polymer and the inflatable expansile member comprises a second amorphous elastomeric polymer which is different than the first amorphous elastomeric polymer In one embodiment the catheter shaft comprises a proximal region, a distal region and a median region between the proximal region and the distal region and wherein the proximal, the median and the distal regions of the shaft comprise materials with differing stiffness.

In one case the proximal region of the catheter shaft comprise a polyamide, the distal region comprises a thermoplastic polyurethane elastomer and the median region comprises a polyether block amide copolymer.

In one case the catheter further comprises an expansile marker band at or adjacent to the expansile member.

In one embodiment the distal marker band is located beneath the expansile member.

In one case the radiopaque distal marker is of generally tubular shape having axially extending slots which are configured to facilitate expansion of the marker.

In one embodiment the clot capture catheter comprises two to more expansile members.

In a further embodiment at least some of the expansile members have differing compliance.

In one case a clot capture catheter comprises inflatable balloon members mounted on the distal section of the catheter, the balloon member comprising an inner balloon members positioned within an outer balloon.

In one embodiment the elastic compliance of the balloon members are different.

In one case only the inner balloon communicates with an inflation lumen facilitating expansion.

In one embodiment the inner balloon is configured to contact the outer balloon, on expansion.

In one case, in the expanded configuration, an effective diameter of the distal-most portion of the expansile member is at least 20%, greater than the diameter of the inner lumen at the distal end of the catheter shaft.

In another case the effective diameter is at least 30%, at least 40%, at least 50%, at least 60%, at least 70%, at least 80%, at least 90%, or at least 100% greater than the diameter of the inner lumen at the distal end of the catheter shaft.

In one embodiment the distal tip region of the expansile member is flared outwardly from the catheter shaft lumen at an opening angle.

In one case the opening angle is from 10 to 60 degrees, or from 15 to 45 degrees.

In one embodiment the expansile member comprises features such as an undulation and/or a fold to assist in flaring of the distal tip region.

In one case the inflatable member is inverted and joined to the catheter shaft at a proximal joint area and wherein the shaft comprises multiple layers, including an outer sleeve, a middle layer, an inner liner, and a reinforcing braid or coil.

In one embodiment the proximal end of the inflatable member is joined to the elongate shaft at proximal joint area and the other end of the inflatable member is inverted and joined to the middle layer at a junction such that the middle section of a generally tubular polymer member that forms the expansile member is positioned at the distal end of the catheter, and the portion of the tubular polymer member that lies between the junction and the middle section is joined to the distal section of the catheter shaft.

In one case a strip of material is mounted over the expansile member and joined proximally to the catheter body and the distal end of the material strip is bonded to the atraumatic distal catheter tip.

In one embodiment a plurality of material strips are positioned radially around the balloon.

In one case the material strip comprises a low elastic compliance polymer such as PET.

In one embodiment the expansile element is of composite construction comprising semi-rigid ribs interspersed with sections of elastic expansile material.

In one case the ribs extend parallel to the axis of the catheter. The ribs may extend in a spiral configuration.

In one embodiment the catheter comprises a sealed inflation chamber which is adapted to be filled with a radiopaque fluid.

In one case a clot capture catheter comprises a plunger for inflating the expansile member and deflating the expansile member.

In another case a clot capture catheter comprises a controller for moving the plunger to control the inflation and deflation of the expansile member.

The controller may comprise a manual knob.

In one embodiment the plunger is defined by a corrugated body.

In one case a clot capture catheter comprises a spring to bias the movement of the corrugated body.

In one embodiment the profile of the distal tip of the expansile member in the expanded configuration is of non-uniform shape.

In one case the profile comprises an ellipse.

In one embodiment a kit comprises a clot capture catheter, a clot engaging device and a microcatheter for the clot engaging device.

The clot engaging device is a stent-retriever device.

In another aspect the invention provides clot capture procedure comprising:
 providing a clot capture catheter having an inflatable member at the distalmost tip of the catheter;
 with the inflatable member in a collapsed configuration, advancing the clot capture catheter towards a clot;
 inflating the inflatable member at the distal tip of the catheter so that the inflatable member extends outwardly from the distalmost tip of the catheter to the vessel wall;
 drawing the clot into the catheter;
 deflating the inflatable member; and
 withdrawing the catheter.

In one case the method comprises aspirating to draw the clot into the catheter. Alternatively or additionally, the method comprises engaging the clot with a mechanical device such as a stent-retriever to draw the clot into the catheter.

In one embodiment a clot capture procedure comprises providing a microcatheter, advancing the microcatheter through the clot capture catheter, and deploying the clot engaging device from the catheter.

In another aspect the invention provides a method for capturing clot comprising: —
 advancing a catheter through the vasculature to a position proximal of the target clot in a vessel;
 crossing the clot with a microcatheter;
 advancing a clot capture device through the microcatheter to the site of the clot;
 retracting the microcatheter to deploy the clot capture device at least partially beneath the clot;
 inflating the expansile member of the catheter to slow or stop flow in the vessel;
 retracting the clot capture device proximally towards the catheter;
 connecting a syringe or pump to the proximal end of catheter and aspirating to reverse blood flow in the vessel;
 retracting the clot capture device and captured clot under aspiration into the mouth of the catheter;
 continuing to retract the clot capture device under aspiration through and out of the catheter; and
 discontinuing aspiration and deflating the expansile member in order to restore blood flow to vessel.

BRIEF DESCRIPTION OF THE DRAWINGS

The invention will be more clearly understood from the following description of some embodiments thereof, given by way of example only, with reference to the accompanying drawings, in which:

FIGS. 3a-3e are sectional views through the shaft and portions of the shaft of a clot retrieval catheter of the invention;

FIG. 4 is a side view illustrating one method of manufacture of a catheter shaft;

FIG. 5 is a sectional view of a distal portion of a clot retrieval catheter of the invention;

FIGS. 6a-6b are sectional views of a distal portion of a clot retrieval catheter of the invention;

FIG. 18a is a simplified view of a distal portion of a clot retrieval catheter of the invention;

FIG. 18b is a cross sectional view on the line A-A in FIG. 18a;

FIGS. 18c-18d are sectional views through the distal portion of a clot retrieval catheter of this invention;

DETAILED DESCRIPTION

Specific embodiments of the present invention are now described in detail with reference to the Figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, diagnostic catheters and microcatheters are described elsewhere and are regularly used in cath lab procedures. It is assumed in the descriptions below that these products and methods are employed in conjunction with the device and methods of this invention and do not need to be described in detail.

The following detailed description is merely exemplary in nature and is not intended to limit the invention or the application and uses of the invention. Although the description of the invention is in many cases in the context of treatment of intracranial arteries, the invention may also be used in other body passageways as previously described.

Figure 1:
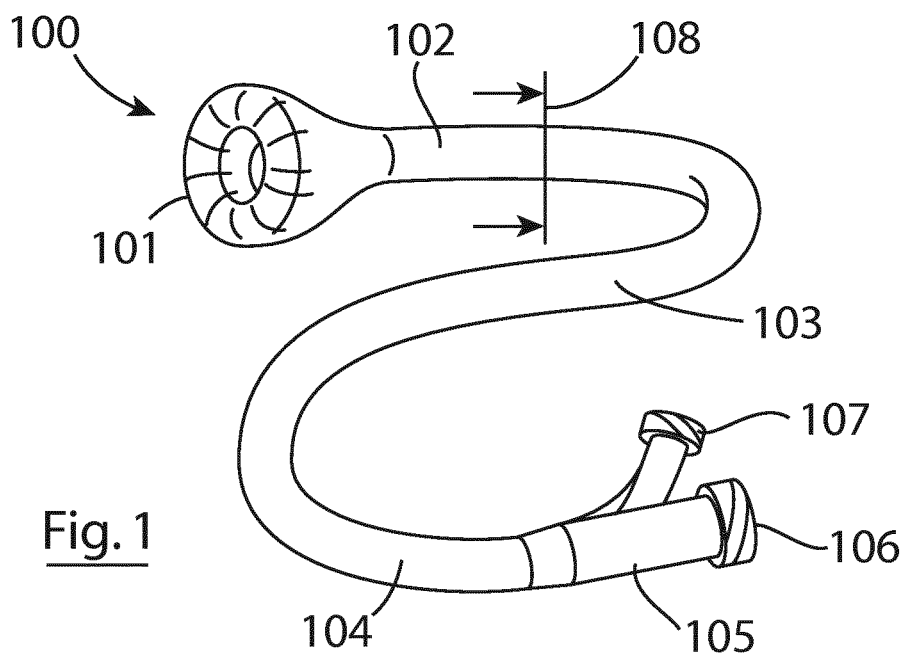
FIG. 1 is an isometric view of a clot retrieval catheter of this invention.

FIG. 1, reference numeral 100 illustrates a clot capture catheter of the invention which comprises a distal inflatable portion 101, attached to a distal shaft 102, which is in turn attached to a shaft mid-section 103, which is attached to a shaft proximal section 104. A proximal hub 105 is connected to the proximal end of the catheter shaft and comprises a luer attachment 106 and a side port 107. Side port 107 provides access to an inflation lumen running through the wall of the catheter shaft from the hub to the inflatable portion 101. The inflation lumen is illustrated in sectional views of the shaft shown in FIG. 2.

The inflatable portion 101 of the distal tip preferably comprises an amorphous elastomeric polymer, so that it can be stretched/strained under inflation pressure to a diameter at least twice and as much as 5 times its uninflated diameter and recover most or all of its unexpanded shape upon deflation. This requires the material to withstand an elastic strain of at least 200% and ideally 500% or more, ideally with minimal levels of plastic deformation or hysteresis. Recoverable strains of such a high level are greatly facilitated by crosslinking of the polymer chains, and hence thermoset materials such as silicone rubbers may be a good choice. However silicone is not an easy material to join to a second material as it cannot easily be melted and made miscible with another material to form a strong and low profile weld joint for example. For this reason polyurethane elastomers are also a suitable material for the balloon of this invention. In particular thermoplastic polyurethane elastomers would make ideal materials as these can be melted as part of a welding or joining process, or can be solvent bonded or adhesively bonded.

Figure 2A:
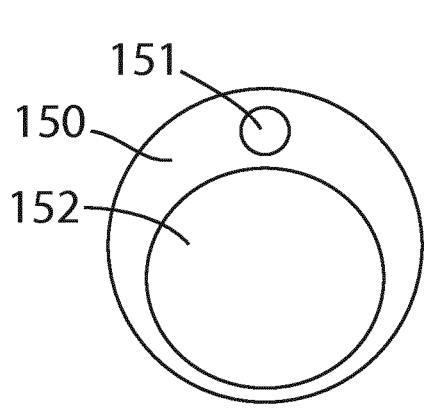
FIGS. 2a-2d are sectional views through the shafts of clot retrieval catheters of the invention.
Figure 2B:
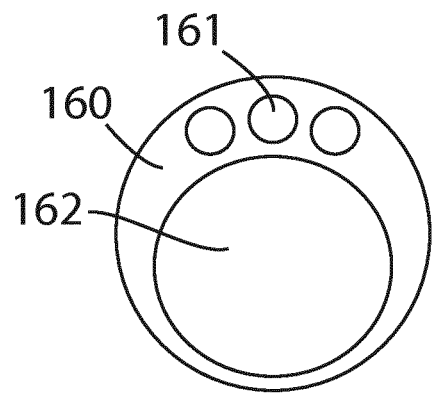
Figure 2C:
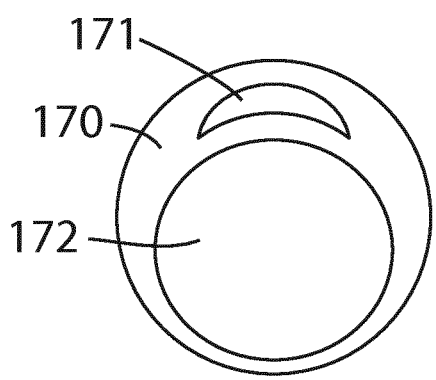
Figure 2D:
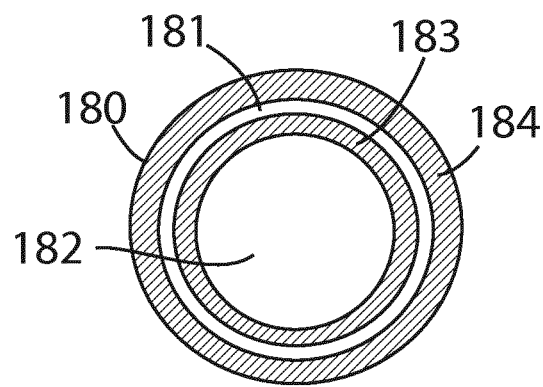

FIGS. 2a-2d illustrate a number of possible sectional views through various embodiments of the shaft of the catheter of FIG. 1, as indicated by section line 108 in FIG. 1. FIG. 2a shows a shaft 150 with an inner lumen 152 and a single inflation lumen 151. FIG. 2b shows a shaft 160 with an inner lumen 162 and three inflation lumens 161. FIG. 2c shows a shaft 170 with an inner lumen 172 and a single oblong, crescent shaped inflation lumen 171. FIG. 2d shows a shaft 180 with an outer shaft wall 184, an inner shaft wall 183, and an internal lumen 182. The space between the inner and outer shaft walls creates the inflation lumen 181. In all of these shaft variants the shaft construction may also comprise a low friction coating or liner (such as PTFE) on the inner lumen wall. Reinforcing braid and/or coil wires or fibers may be used to provide hoop strength (to withstand aspiration through the inner lumen without collapse) and kink resistance. The main wall of the shaft may comprise one or more materials, with thermoplastic polymers such as Polyurethane, Pebax and Polyamide being examples of preferred options. In one example of a preferred shaft material configuration one or more grades of polyurethane are used for the balloon and very distal section of the catheter; one or more Pebax (polyether block amide copolymer) materials are used for a mid-section of the catheter; and one or more polyamide material(s) are used for the proximal section of the catheter shaft. This series of materials offers increasingly higher durometers and Young's modulus (or stiffness), so that a very flexible distal shaft region can be smoothly transitioned to a much stiffer proximal shaft region. The Polyether block amide material has the advantage of being joinable to both the Polyurethane and the Polyamide, even though the Polyurethane and the Polyamide are not so easily joined to one another.

The inflation lumen may be formed in a number of different ways as will be described later, and may be lined with a material or materials (such as PTFE, FEP, PET or Polyimide for example), of a higher melting point or softening point to that of the main wall of the shaft in order to facilitate formation of the inflation lumen and subsequent removal of any forming mandrels used in that process. The shaft may be eccentric in design as shown in FIGS. 2a-2c in order to provide sufficient wall thickness to create an inflation lumen without creating an excessive overall catheter diameter. Alternatively, a concentric design such as that illustrated in FIG. 2d may be employed.

FIGS. 3a-3e show a series of sectional views through portions of a shaft of the clot retrieval catheter of this invention, illustrating how one embodiment of the inflation lumen might be formed. In this embodiment elongate tube 200 of FIG. 3a is fitted with three mandrel wires 201, causing the tube to deform into an oblong shape as shown in FIG. 3b. The assembly of tube 200 and wires 201 is then placed on top of an elongate shaft 203, and an outer jacket 202 is placed over both as shown in FIG. 3c. Heat and pressure are then applied (optionally through another outer jacket or heat shrink tuning, not shown) as indicated by lines 204, in order to laminate the entire assembly together. This process fuses the outer jacket 202 to the inner elongate shaft 203 and surrounds the inflation lumen tube 200 with its internal mandrel wires 201 as shown in FIG. 3d. The mandrels serve the purpose of preventing collapse of the inflation lumen during this forming process, and maintaining its desired shape. Once the forming process is completed the mandrels are removed, leaving the inflation lumen 206 open and unobstructed through the composite shaft 205 as shown in FIG. 3e. Many variants of this design and process are possible—for example the inflation tube could be made from a low friction material such as PTFE, in which case it could be either left in place upon removal of the mandrel wires, or it could be removed itself with or after the mandrel wires. In another embodiment the inflation tube is made by solution casting and comprises a polyimide or other relatively high modulus material, which can be manufactured in a wall thickness of as little as 0.001" or lower and still maintain a high degree of structural integrity. Another advantage of polyimide as a material choice is that it will not melt during the catheter forming/fusing process, minimizing the challenge of mandrel removal at the end. The mandrels themselves may be metallic or formed from a very high tensile polymer, and are ideally coated with a low friction material such as PTFE or Parylene.

FIG. 4 illustrates a preferred method of manufacture of the catheter shaft of this invention. An interface between two lengths of polymer tubing (251 and 252) of different durometers and/or modulus of elasticity, are illustrated being joined together at a point along the shaft length by a heat and pressure forming process involving an external heat shrink tube 252 and a heat source 253. It is desirable the catheter shaft have a stiffness gradient along much of its length in order to transition seamlessly from a stiff and pushable proximal end to a highly flexible and atraumatic distal end. It is not desirable that this stiffness gradient be abrupt, which can be a problem at a junction between two shaft materials. Feathering the ends of the tubing to be joined as shown in region 254 creates a more gradual stiffness transition from a first material 250 to a second material 251. In this way the % of each material in a given cross section of shaft can be varied over a greater length than would be possible by the minimal amount of material mixing that would occur in a simple butt joint. The construction shown enables overlap area 254 to extend to greater than 10 mm in length if desired, but an overlap length of between 1 mm and 5 mm is preferred.

FIG. 5 shows a sectional side view of the distal end of a clot retrieval catheter 300 similar to catheter 100 shown in FIG. 1. The catheter comprises a substantially cylindrical elongate tubular shaft 302, to which is mounted an inflatable distal balloon 301. Distal balloon 301 is configured in such a way as to create a funnel shaped profile upon expansion. This funnel shaped profile may be attained by the position and wall thickness profile of the expansile membrane forming the balloon, and/or may be attained by the use of addition elements to help flare the catheter tip as explained in more detail elsewhere in this document. Line 303 denotes the centerline of the catheter tip region. Lines 305 and 306 are lines parallel to centerline 303 indicating the diameter 311 of the opening at the distal-most face of the catheter. Points 309 and 310 indicate where lines 305 and 306 intersect distal face 304, indicating the extent of the open diameter of the distal end of the catheter. Lines 307 and 308 are lines parallel to centerline 303 indicating the diameter 312 of the inner lumen of the catheter into which clot must ultimately be squeezed in order to remove it fully through the catheter.

The critical feature of this profile is that the effective diameter 311 of the distal-most portion of the catheter is significantly greater than the diameter 312 of the generally cylindrical inner lumen of the distal region of the catheter. Conventional clot retrieval catheters may have some rounding or chamfering of their distal tips to create a very minor lead-in, but this has minimal effect of reducing the shear stress on clot and avoiding fragment loss. The invention disclosed creates a genuine funnel shape without the need for a pull-wire or other such stiff and bulky mechanical actuation. The funnel created is such that diameter 311 is ideally at least 20% greater than diameter 312, and preferably 50% or 100% greater than diameter 312. Thus if diameter 312 is 0.084" as might be the case for a typical catheter of this type, then diameter 311 is at least 0.101" and is ideally as much as 0.126" or 0.168" or more.

Figure 7A:
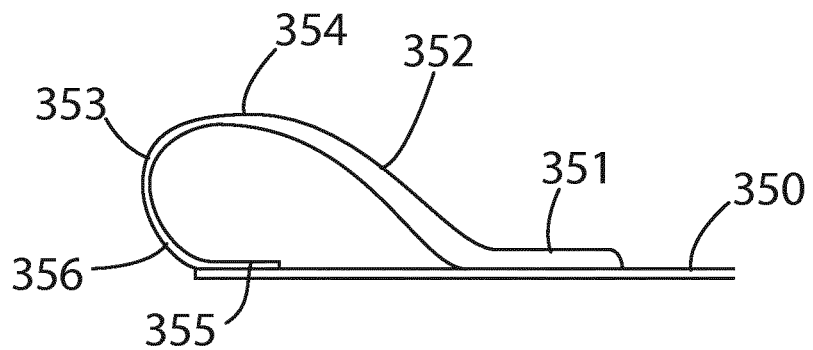
FIGS. 7a-7c are sectional views of distal portions of clot retrieval catheters of the invention.
Figure 7B:
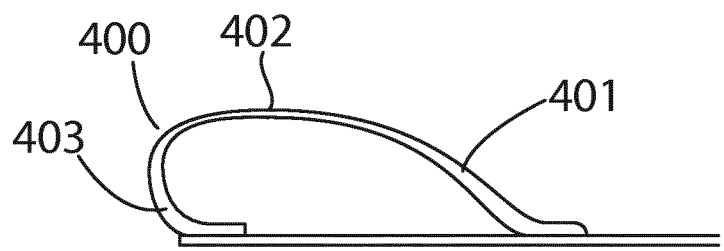

The wall thickness profile of the inflatable member 301 is very similar to that of inflatable member 400 of FIG. 7b, and the description provided therein may be referred to.

FIGS. 6a and 6b show simplified sectional views of the distal region of a clot retrieval catheter of this invention in the inflated and uninflated states respectively. The catheter comprises an elongate shaft 320 with an inner liner 323, a distal tip section 326 and an inflatable portion 328. The inflatable portion 328 has different wall thicknesses in different regions in order to create the desired shape and effect upon inflation. Low wall thickness region 321 experiences the highest strain and consequently expands the most upon inflation, creating a balloon-like shape that can be used to restrict or prevent blood flow from passing the catheter. High wall thickness region 322 undergoes much lower strain at the same stress (and pressure) levels, and hence cannot expand to the same diameter as the lower wall thickness region, however it is placed under axial tension by the pressure within the inflated member, and this tension pulls on and helps to flare the tip section 326 to an opening angle 330. Opening angle 330 is preferably between 10 and 60 degrees, and is most preferably between 15 and 45 degrees. Thin wall thickness region 327 acts as a hinge to minimize the resistance to flaring of the tip. Further features such as folds or undulations may also be provided to this region to assist in tip flaring—an example of this is provided in FIG. 16. A further thin wall hinge (not shown) may be provided at region 329 to assist in the flaring of the tip region into a funnel-like shape. A marker band 324 is shown beneath the inflatable portion, which serves a dual purpose of providing visibility of the catheter tip under fluoroscopy and also of providing hoop strength to the catheter shaft to prevent deformation under inflation pressure.

Figure 7C:
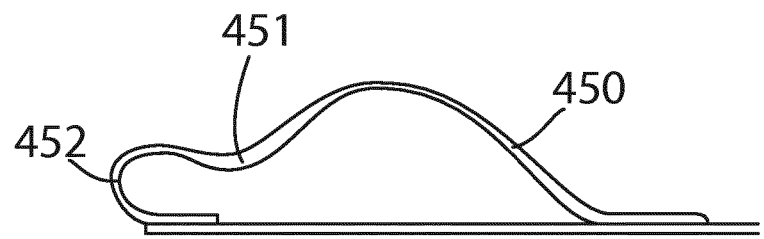

FIGS. 7a-7c show simplified section views through the distal portion of clot retrieval catheters of this invention, illustrating how varying the wall thickness profile of the inflatable portion of the catheter can be used to influence the shape of the inflated balloon.

In FIG. 7a the proximal neck 351 of inflatable member 354 comprises a first thickness, and is connected to catheter shaft 350 proximal of the distal end of the catheter. The proximal portion 352 of the inflatable member comprises a second thickness, while the distal portion 353 comprises a third thickness, and the distal neck 355, which is inverted and joined to the distal end of the catheter shaft 350, comprises a fourth thickness. The mid portion 356 of the inflatable member 354 comprises a variable thickness which tapers from the second thickness 352 to the third thickness 353. In one embodiment the first thickness is greater than the second thickness, and the second thickness is greater than the third thickness. In one embodiment the fourth thickness is greater than the third thickness. In one embodiment the fourth thickness is greater than the first thickness. In one embodiment the first thickness is generally equal to the second thickness in the deflated state, but is greater than the second thickness in the inflated state. This thinner profile of the distal section of the inflatable member causes that section to preferentially inflate and expand distally, creating the desired funnel shape cross section. However over-inflation of such a profile may result in the distal section 356 impinging on the lumen of the catheter, a problem which is solved by the profile illustrated in FIG. 7b and elsewhere in this document.

FIG. 7b shows another embodiment of the distal portion of a clot retrieval catheter of this invention, with a slightly different wall thickness profile. In this case the wall thickness of the proximal 401 and distal 403 portions of the inflatable member 400 is greater than that of the mid 402 portion. This thinner profile of the middle section of the inflatable member causes that section to preferentially inflate radially, which causes an axial strain in the proximal and distal sections. This axial strain lifts and flares the distal portion 403, creating the desired funnel shaped profile.

FIG. 7c shows another embodiment of the distal portion of a clot retrieval catheter of this invention, with a slightly different wall thickness profile. In this case a band 451 of greater wall thickness is provided between the proximal and distal regions of balloon 450, to create a relatively non-expansile region 451, forcing the balloon to preferentially inflate proximal and distal of that band, thus creating a distal "bulge" 452 and hence the desired funnel shape profile.

In each of these embodiments the wall thickness of the thinner walled sections decreases by a greater % upon inflation than does the wall thickness of the thicker walled sections, which enables the uninflated wall thickness to be used to control the inflated shape of the inflatable member.

Figure 8A:
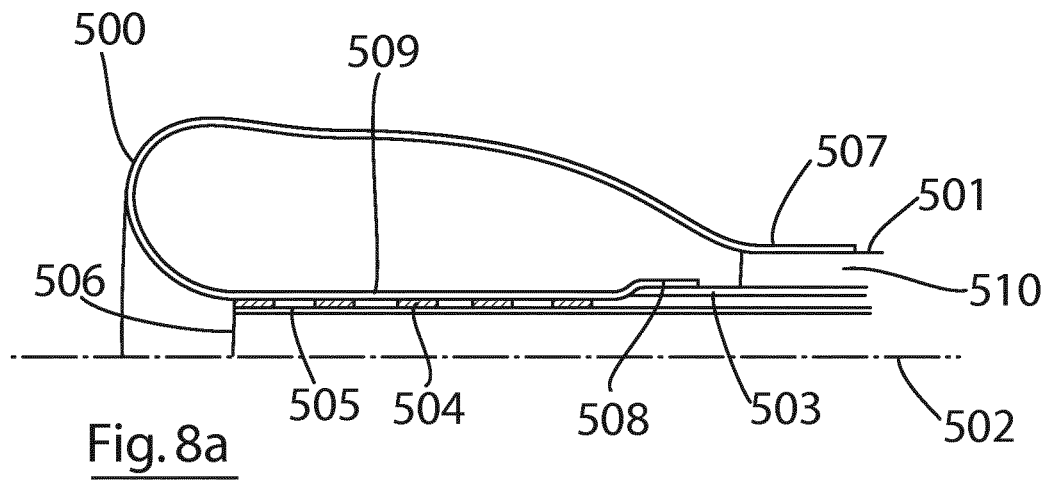
FIGS. 8a-8c are sectional views of distal portions of clot retrieval catheters of the invention.
Figure 8B:
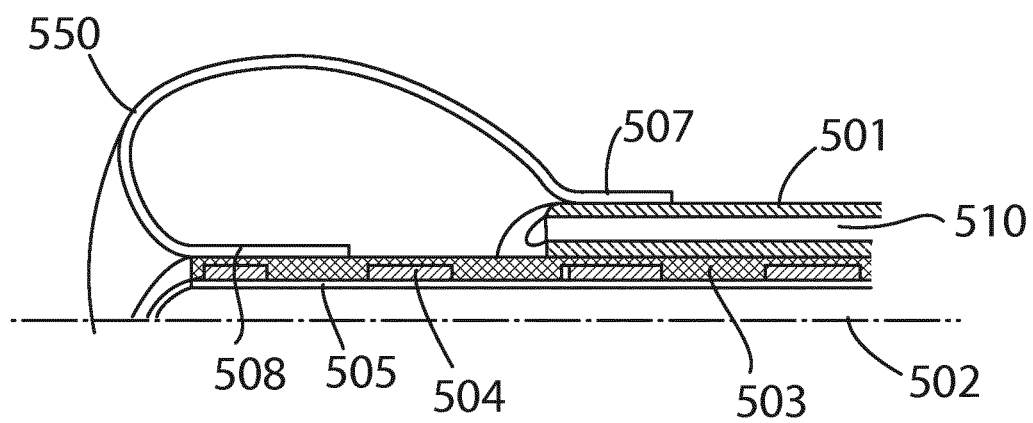
Figure 8C:
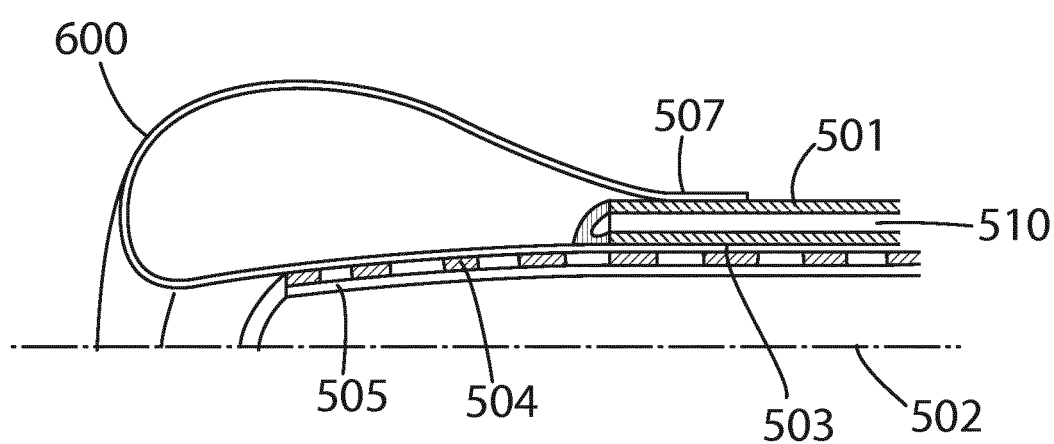

FIGS. 8a-8c show partial section views around centerline 502 through the distal portion of clot retrieval catheters of this invention, illustrating examples of how an inverted member (tubular or otherwise) can be used to form the inflatable member of the catheter.

FIG. 8a shows inflatable member 500, which is joined to elongate shaft 501 at proximal joint area 507. Shaft 501 comprises multiple layers, including an outer sleeve 510, a mid-layer 503, an inner liner 505, and a reinforcing braid or coil 504. Shaft 501 also comprises an internal inflation lumen (not shown) as described elsewhere. The inflatable member 500, the catheter outer sleeve 510 and the catheter mid-layer 503 are preferably all made from either the same family of materials (such as polyurethanes for example) or at least from materials with compatible components, so that they can be joined together through a heat and pressure or solvent bonding process. The proximal end of inflatable member 500 is joined to elongate shaft 501 at proximal joint area 507, while the other end of inflatable member 500 is inverted and joined to middle layer 503 at junction 508. Thus the middle section of the generally tubular polymer member 511 that forms inflatable member 500 is positioned at the distal end of the catheter, and the portion 509 of the tubular polymer member 511 that lies between junction 508 and the middle section is laminated onto the distal section of the catheter shaft (comprising the inner liner and reinforcing braid or coil.

FIG. 8b shows a very similar construction to that shown in FIG. 8a, except that in this case inflatable member 550 has a shorter inverted length, and the mid layer 503 of shaft 501 extends substantially to the distal end of the catheter liner and braid. Thus the junction 508 between the inverted portion of inflatable member 550 and the shaft can be made closer to the distal end of the catheter.

FIG. 8c shows a very similar construction to that shown in FIG. 8a, except that in this case inflatable member 600 is formed from an extended inverted portion of the mid-layer 503 of the shaft 501.

FIGS. 9a-9d (prior art) illustrate one of the big problems with conventional balloon guide catheter technology that can cause serious patient harm during a clot retrieval procedure.

Figure 9A:
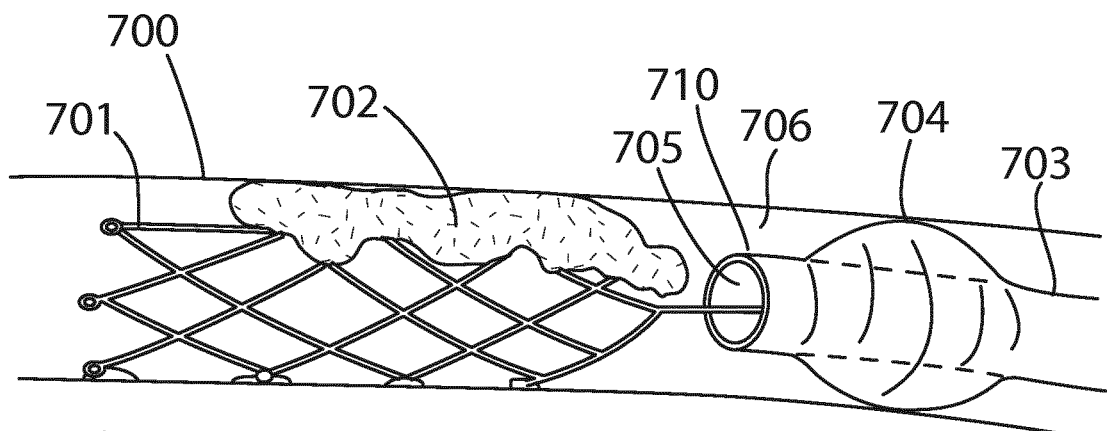
FIGS. 9a-9d are views of a conventional prior art thrombectomy procedure.

FIG. 9a shows a clot retrieval device such as a stent-retriever 701 retrieving a clot or thrombus 702 through vessel 700 into the distal mouth 705 of balloon guide catheter 703. Balloon guide catheter 703 comprises a balloon 704 positioned just proximal of its distal tip portion 710. A typical thrombectomy procedure involving a stent-retriever involves:

Using conventional endovascular access techniques to advance the balloon guide catheter 703 (or similar guide or sheath) through the vasculature to a position proximal of the target clot;

Crossing the clot with a microcatheter, usually with the aid of a guidewire;

Advancing a stent-retriever through the microcatheter to the site of the clot;

Retracting the microcatheter to deploy the stent-retriever at least partially beneath the clot;

Inflating the balloon 704 of the balloon guide catheter 703 in order to slow or stop flow in the vessel 700;

Retracting the stent-retriever proximally towards the balloon guide catheter;

Connecting a syringe or pump to the proximal end of balloon guide catheter 703 and aspirating in order to reverse blood flow in vessel 700;

Retracting the stent-retriever and captured clot under aspiration into the mouth 705 of the balloon guide catheter 703;

Continuing to retract the stent-retriever under aspiration through and out of the balloon guide catheter 703;

Discontinuing aspiration and deflating balloon 704 in order to restore blood flow to vessel 700.

FIG. 9a illustrates the stage of this procedure in which the stent-retriever 701 and clot 702 are about to be withdrawn into the mouth 710 of balloon guide catheter 703. Balloon 704 is inflated and the operator has commenced aspiration through the balloon guide catheter 703 in order to reverse blood flow in vessel 700 and assist in withdrawing the clot safely into the mouth 710 of the catheter. However because the tip 710 extends distally of the distal end of the balloon 704 there exists a dead space 706 around the distal tip 710 just distal of the balloon 704. In which there is little or no reverse flow to pull the clot or any clot fragments into the catheter mouth.

Figure 9B:
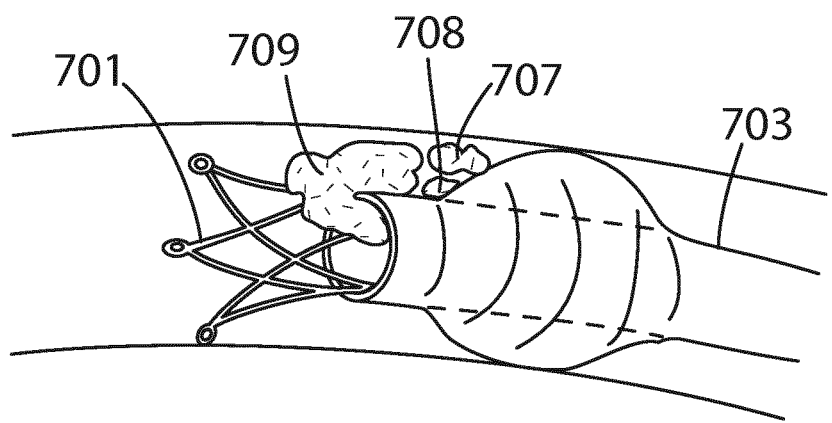

FIG. 9b illustrates the stage of the above procedure in which the stent-retriever 701 and clot 702 are being withdrawn into the mouth 710 of balloon guide catheter 703. As the clot is pulled into the catheter it must deform in shape in order to fit into the catheter lumen. The level of deformation required depends on the relative size of the clot and catheter lumen, and also on the degree to which the stent-retriever compresses the clot against the catheter. Greater levels of deformation give rise to greater levels of shear stress on the clot, which are often concentrated at the tip of the catheter, as that is where the clot undergoes an abrupt shape change. This can cause the clot to tear and release fragments, particularly if the clot does not have a very organized fibrin structure and/or if a lytic drug such as tPa has been given to the patient. In this case clot fragments 707 and 708 have been released from the clot and are sitting in the dead space 706, and the shear stresses on the clot have induced an overhang region 709 which has been pushed proximal of the distal mouth 705 of the catheter and is at risk of tearing free from the main body of the clot.

Figure 9C:
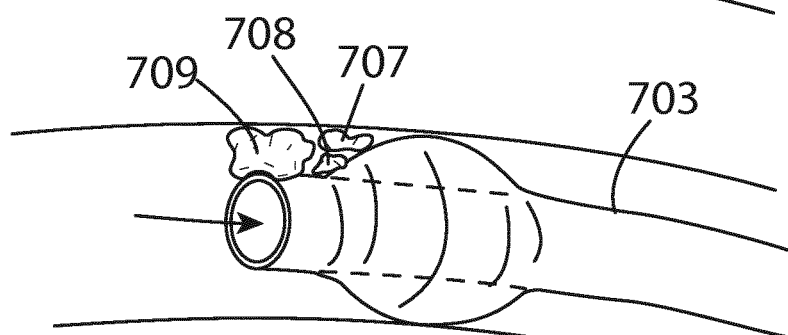

FIG. 9c shows the consequences of the previously described high shear forces combined with dead space 706: clot fragments 707 and 708 that were shown in FIG. 9b have been joined by a third fragment 709, and the reverse flow through the vessel into the catheter induced by the aspiration has failed to pull them out of the dead space and into the catheter mouth.

Figure 9D:
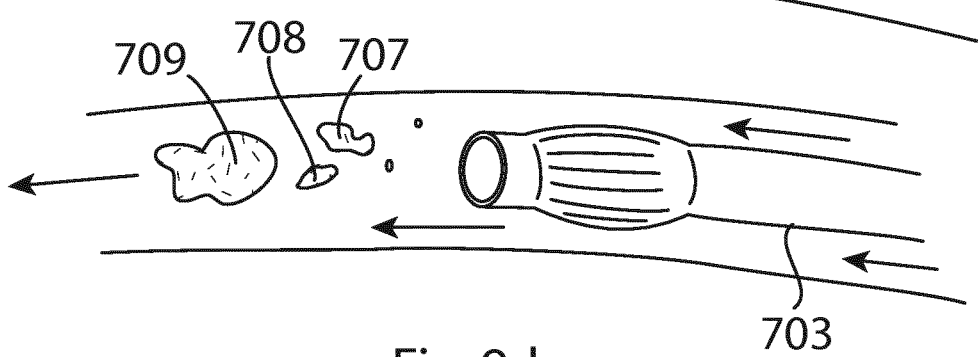

FIG. 9d shows a later stage in the procedure after removal of the stent-retriever 701 and any captured clot from within the catheter 703. At this stage aspiration through the catheter is stopped and the balloon 704 is deflated. This results in restoration of blood flow to the vessel 700 distal to the catheter, and consequently clot fragments 707, 708 and 709 are released and flow downstream, where they are likely to occlude one or more vessels, potentially causing serious patient harm or even death.

Any suitable clot capture device can be used as part of the kit and the procedures described herein. The clot capture device may be of a stent-retriever type. The clot capture device may be as described in any of our WO2012/120490A, WO2014/139845A, WO2016/083472A and/or WO2017/089424A.

FIGS. 10a-10d illustrate a similar thrombectomy procedure to that shown in FIGS. 9a-d, but this time employing a clot retrieval catheter 803 of this invention. The same procedural steps described above are carried out, but because the catheter 803 has the twin advantages of 1) little or no dead space distal to the balloon and 2) a flared distal mouth to minimize shear stress on the clot, in this case the clot is fully retrieved into the catheter and no clot fragments are lost upon balloon deflation.

Figure 10A:
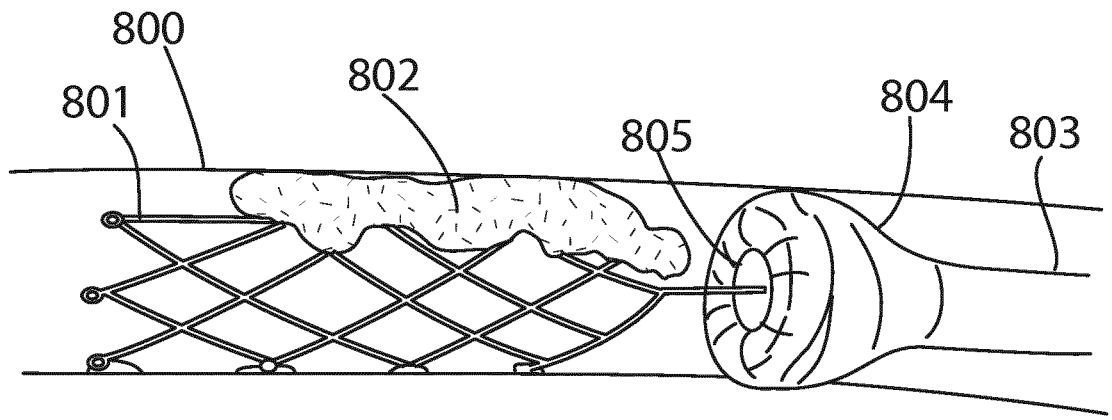
FIGS. 10a-10d are views of a thrombectomy procedure employing a clot retrieval catheter of the invention.

FIG. 10a shows a clot retrieval device such as a stent-retriever 801 retrieving a clot or thrombus 802 through vessel 800 into the distal mouth 805 of clot retrieval catheter 803. Clot retrieval catheter 803 comprises a balloon 804 positioned at its distal end. As described in relation to FIGS. 9a-d above the balloon 804 has been inflated to restrict flow in vessel 800, and aspiration through the catheter 803 may be employed to further assist clot entry into the catheter mouth 805 by reversing blood flow in vessel 800.

Figure 10B:
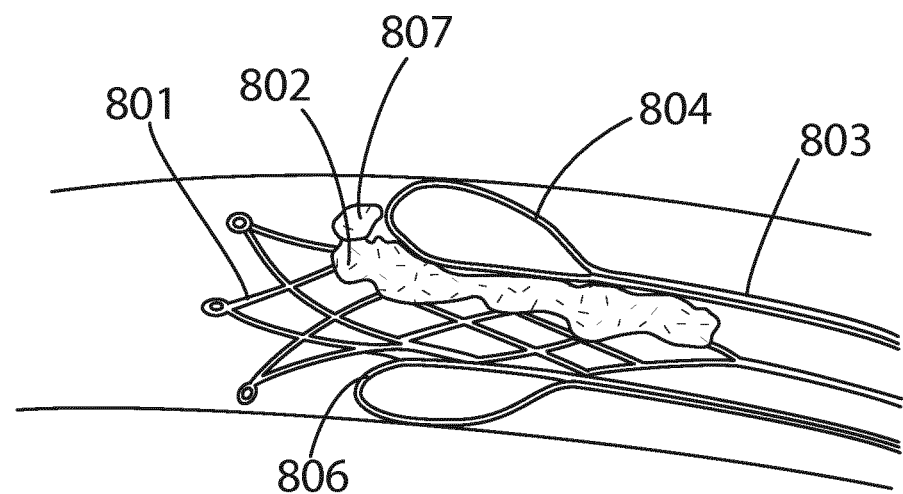

FIG. 10b illustrates the stage of the above procedure in which the stent-retriever 801 and clot 802 are being withdrawn into the mouth 805 of catheter 803. The funnel shaped profile 806 of the catheter 803 minimizes the shear stress induced in the clot as it is withdrawn into the catheter, and any fragments created or otherwise present (such as fragment 807 shown) have little or no dead space between balloon and tip to get caught within.

Figure 10C:
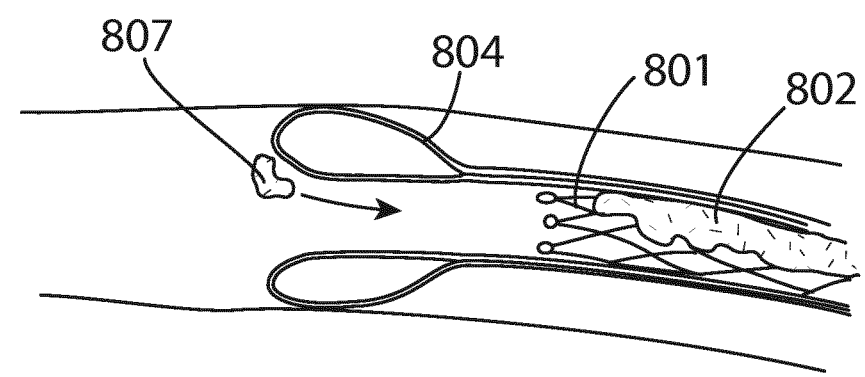

FIG. 10c shows the benefits of this lack of dead space, as the aspiration and flow reversal through the catheter lumen pulls fragment 807 safely into the catheter lumen, following the stent-retriever 801 and main body of clot 802.

Figure 10D:
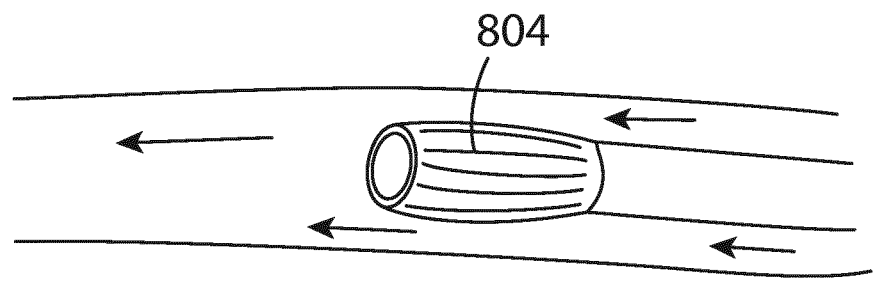

FIG. 10d shows a later stage in the procedure after removal of the stent-retriever 801 and captured clot 802 from within the catheter 803. At this stage aspiration through the catheter is stopped and the balloon 804 is deflated. This results in restoration of blood flow to the vessel 800 distal to the catheter, safely restoring oxygenated blood to the distal vasculature without releasing any harmful clot fragments.

Figure 11:
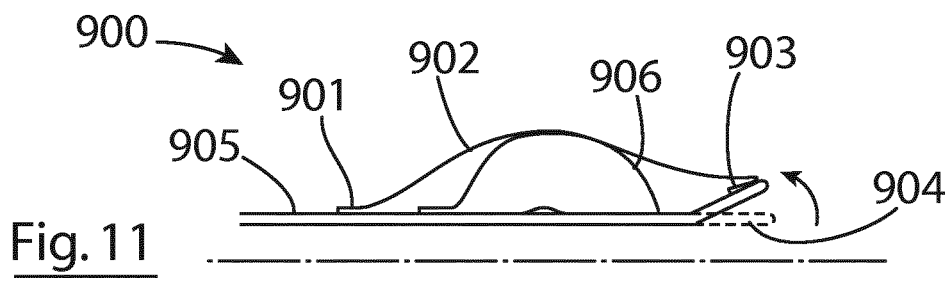
FIG. 11 is a sectional view of a distal portion of a clot retrieval catheter of the invention.

FIG. 11 shows an embodiment of the invention 900 which illustrates a partial section of the distal end of a clot capture catheter. Two inflatable balloon members 902 and 906 are mounted on the distal section of the catheter 905, with one balloon member 906 position within the outer balloon 902. One or both expansile balloon members may communicate with an inflation lumen to allow fluid to be injected into the balloon causing it to expand. The elastic compliance of the two expansile members may vary with the compliance of balloon 902 lower than the compliance of balloon 906 or vice versa. In one case only balloon 906 communicates with an inflation lumen facilitating expansion. When this balloon 906 expands, it occludes the artery or vessel in which it is deployed to improve the efficacy of aspiration and clot retraction into the catheter. In addition as balloon 906 expands it contacts balloon 902 forcing it to expand and increase diameter. The compliance of the balloon 902 ensures that as the diameter increases, the length of the balloon shortens which pulls the distal tip of the catheter 904 into a funnel like shape that facilitates clot retrieval. The bond 903 between the balloon 902 and the distal tip 904 is positioned at or near the distal tip of the catheter to facilitate the forming of the funnel shape. The compliance of one or both of these balloons may differ from the circumferential direction to the longitudinal direction parallel to the catheter axis. This will facilitate preferential expansion in one direction when fluid is injected under pressure through the inflation lumen.

Figure 12:
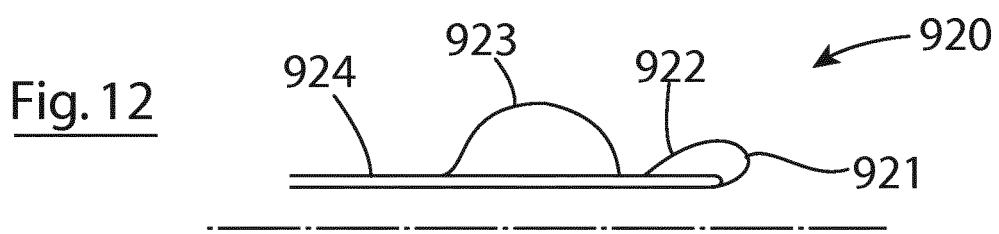
FIG. 12 is a sectional view of a distal portion of a clot retrieval catheter of the invention.

FIG. 12 illustrates another embodiment of the invention 920 with multiple expansile balloons mounted on the catheter. This figure is also a partial section view, and in this embodiment an expansile member 922 is mounted at the distal tip of the catheter 924. The distal expansile member 922 forms a lead-in shape 921 to facilitate clot retraction into the catheter. Mounting multiple balloons or expansile members on the catheter allows the functions of an expansile balloon to be separated and allows different performance attributes to be met by different expansile elements. For example in this case, the distal balloon 922 facilitates clot retrieval and may centralize the catheter tip in the vessel while the balloon 923 occludes the vessel and provides flow arrest. Therefore the distal balloon 922 may have a diameter smaller than the vessel in which the catheter is deployed and may be a 'non-compliant' or low compliance balloon, while the more proximal positioned balloon 923 may be a soft compliant balloon with a larger diameter than the vessel to provide atraumatic vessel occlusion. The distance between the balloons along the axis of the catheter can vary from 2 mm to 150 mm and in the preferred embodiment vary from 2 cm to 10 cm. As the distal balloon has a smaller diameter than the vessel, it may be inflated to a higher pressure without causing any expansile strain to the vessel. This higher pressure could provide the benefit of partially centering the catheter tip in the vessel. Positioning the balloon 923 that provides flow arrest proximal of the catheter tip facilitates designing the catheter so that this balloon is positioned in a more suitable section of the vessel than the location of the distal tip, e.g. a section of the vessel with increased bony or external support. Alternatively the proximal balloon could be positioned in the proximal section of the internal carotid artery or even in the common carotid artery.

Figure 13:
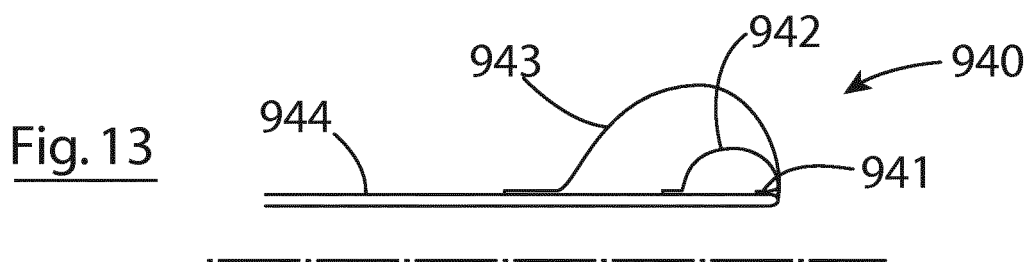
FIG. 13 is a sectional view of a distal portion of a clot retrieval catheter of the invention.

FIG. 13 shows another partial section view of a catheter with multiple balloons. In this embodiment 940, the balloon 942 is located within the balloon 943. Both balloons can communicate with inflation lumens and can inflate simultaneously or individually as desired by the operator. Balloon 942 is a low compliance balloon with a diameter suitable to partially self-center the catheter tip in the vessel. The higher compliance softer outer balloon 943 provides atraumatic occlusion of the vessel providing flow arrest prior to clot aspiration or retrieval. This vessel occlusion can occur with the same pressure in both balloons or an increased pressure can be applied to one of the balloons depending on the phase of the procedure.

Figure 14:
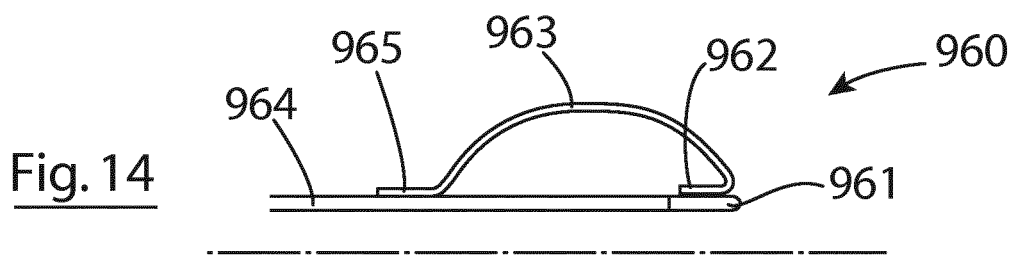
FIG. 14 is a sectional view of a distal portion of a clot retrieval catheter of the invention.

FIG. 14 illustrates a partial section view of a clot retrieval catheter 960 which has an expansile balloon 963 mounted at the distal tip. FIGS. 8 and 9 show the benefits of attaching the balloon at the distal tip of the catheter so there is no 'dead-space' between the distal tip and the balloon and subsequently reduced risk of clot shearing as clot is retrieved into the catheter. FIG. 14 shows how the balloon 963 may be attached to the catheter 964 for optimum positioning at the tip 961 by inverting the neck 962 of the balloon. One method of assembly is to bond or weld the neck of the balloon 962 to the tip of the catheter 961, then invert the balloon and join the proximal neck 965 of the balloon to the catheter 964. Joining the balloon to the catheter in this way not only reduces clot shear it also allows the atraumatic tip of the catheter 961 to flare and act as a lead-in for the clot during clot retrieval.

Figure 15:
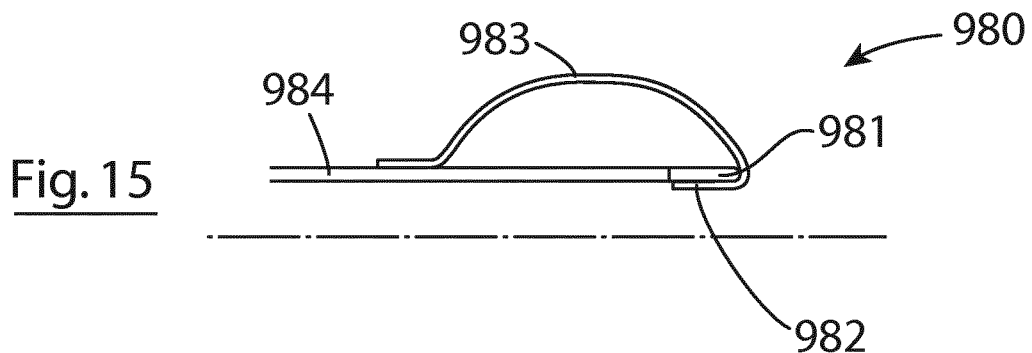
FIG. 15 is a sectional view of a distal portion of a clot retrieval catheter of the invention.

FIG. 15 shows a similar balloon catheter construction to that shown in FIG. 14. However in this embodiment 980, the distal neck 982 of the balloon 983 is attached to the inner surface of the catheter tip 981. In this design the bonding of the distal neck 982 may be completed before or after the proximal neck bond by inverting the balloon neck inside the catheter.

Figure 16A:
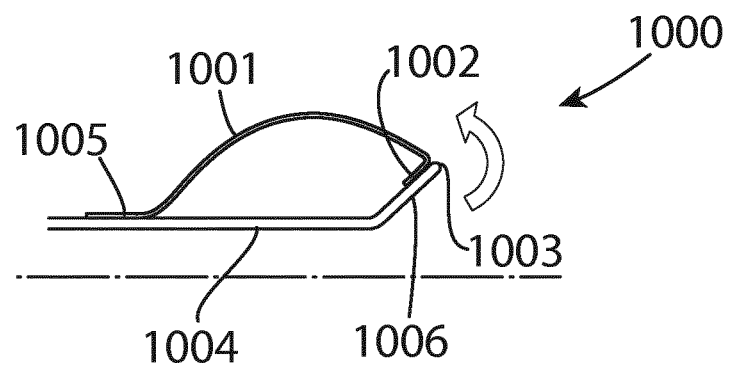
FIG. 16a-16c are sectional views of a distal portion of a clot retrieval catheter of the invention.

FIG. 16a is a partial section view of the distal end of invention 1000 showing a schematic of an expansile member 1001 mounted on the catheter shaft 1004. The expansile element 1001 is joined to the catheter proximally at 1005 and at the distal tip 1003 of the catheter. The neck of the expansile element 1002 is shown inverted at the join to the tip 1003 so that the element 1001 expands fully to the tip 1003 reducing the risk of clot shearing as discussed elsewhere in this patent. In addition, as the element 1001 expands it applies tension to the catheter tip 1003. In this embodiment the distal tip section 1006 has a lower bending stiffness than the catheter section 1004 so that the tip 1003 can flare and expand into a funnel shape under tension, to facilitate improved clot retrieval performance.

Figure 16B:
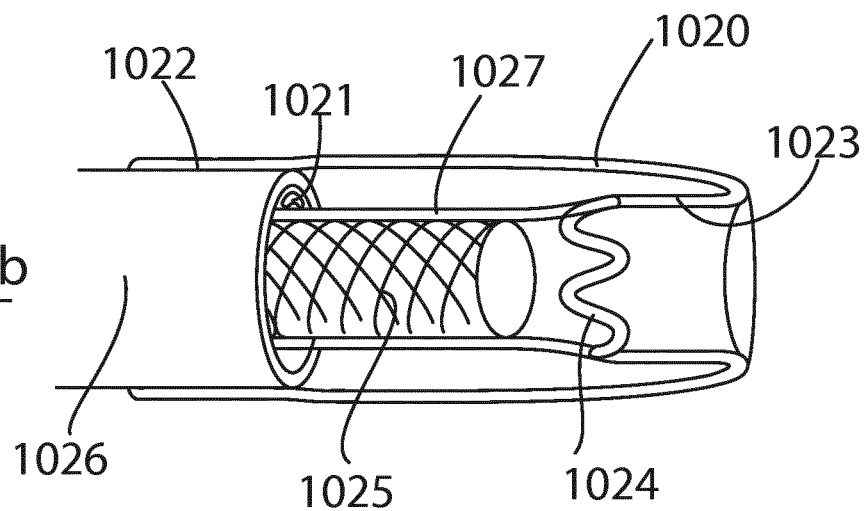

FIG. 16b shows a cut-away illustration of a distal catheter construction similar to the device shown in the schematic image in FIG. 16a. The expansile element in this embodiment is a balloon 1020 which is joined to the catheter 1026 at the proximal end of the balloon 1022. The distal end of the balloon is inverted and welded to the catheter material 1027 to form the distal tip 1023. The catheter 1026 is constructed so that material 1027 protrudes distal of the catheter reinforcement braid 1025 and is under the inflation lumen 1021. The inflation lumen 1021 provides a channel for fluid to be introduced into the balloon 1020 for expansion. When the balloon is expanded, the tension in the balloon 1020 pulls the tip 1023 (distal of the braid 1025) into a funnel shape to improve the efficacy of clot removal. A distal radiopaque marker 1024 is incorporated into the catheter construction to indicate the position of the distal tip in the vasculature under fluoroscopy. The radiopaque marker 1024 is formed in a shape that can expand easily so that it will not restrict the expansion of the catheter tip 1023.

Figure 16C:
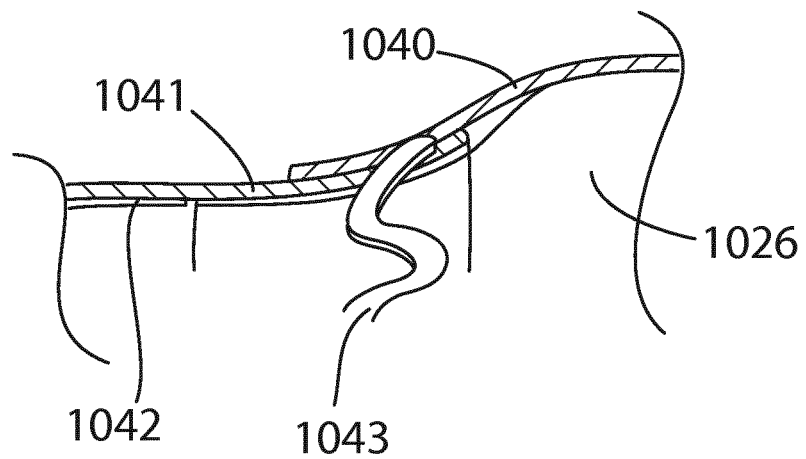

FIG. 16c is a partial section of a distal end of another catheter of the invention. It is shown in the expanded configuration and in this case the balloon neck 1040 is bonded to the catheter material 1041 which protrudes over the liner 1042 and braid. The radiopaque marker 1043 is shown expanded to facilitate the distal catheter tip forming a funnel or lead-in shape 1026.

Figure 16D:
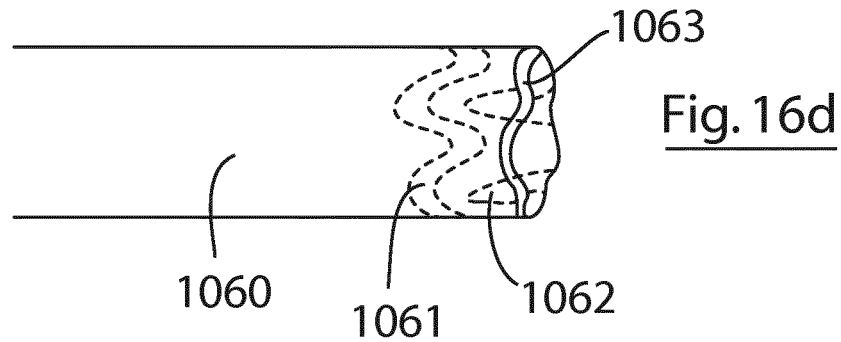
FIG. 16d is a side view of a distal portion of a clot retrieval catheter of the invention.

FIG. 16d shows a distal view of the catheter 1060 with the tip 1063 in the non-expanded configuration. The image shows how the distal tip material may be formed in pleats 1062 to facilitate expansion into a funnel shape when the balloon is expanded. The radiopaque marker 1061 is shaped around the pleats 1062 but still has an expansile capability.

Figure 16E:
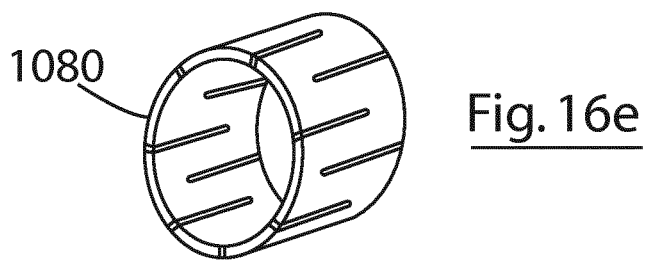
FIGS. 16e-16g are views of one expansile marker band of the invention.
Figures 16F, 16G:
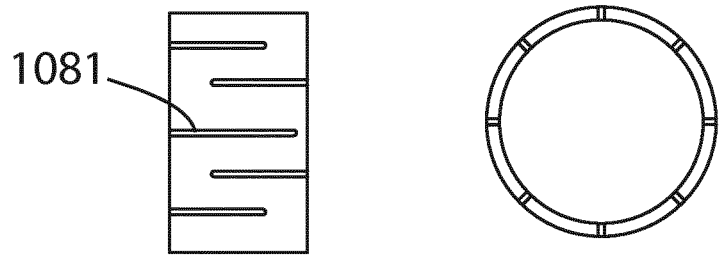

FIG. 16e-16g show an isometric, side and end view respectively of an alternative radiopaque distal marker 1080 for incorporation in the clot capture catheter. This marker is formed of a highly radiopaque material such as gold, platinum or tungsten in a tubular shape with slotted cuts 1081 to allow the marker to expand. Alternatively a gold coated nitinol marker may be used so that it can recover to its original shape after the balloon is deflated. The benefit of this shape of marker is that it can prevent the catheter tip collapsing inwards towards the centerline of the catheter, reducing the aspiration lumen when the balloon is expanded.

Figures 16H, 16I:
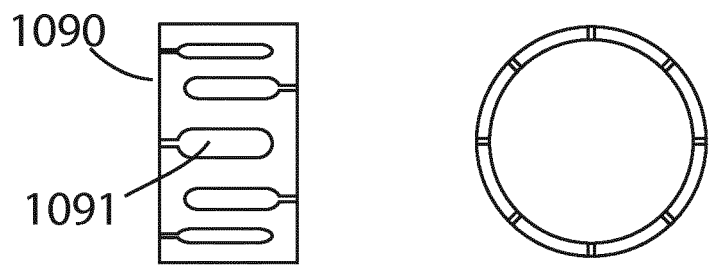
FIGS. 16h-16i are views of another expansile marker band of the invention.

FIG. 16h and FIG. 16i show side and end views respectively of a similar expansile radiopaque marker 1090 with increased slot widths 1091 to improve integration with the catheter tip material. This marker is also expansile while restricting a reduction of diameter when under external pressure. The use of a radiopaque marker or other reinforcement to prevent reduction of the inner diameter when the balloon is inflated, allows softer catheter tip materials to be used.

Figure 17A:
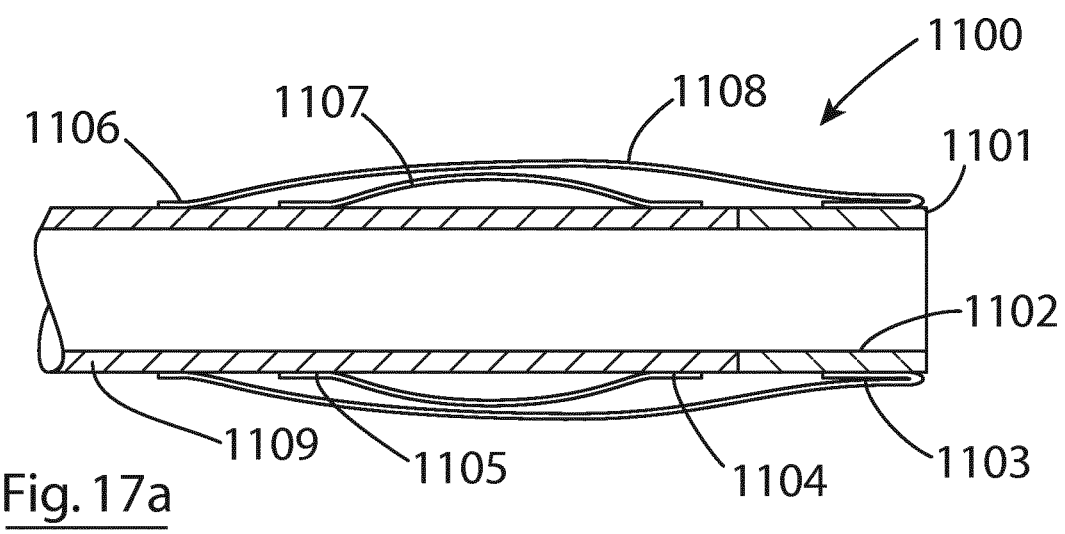
FIG. 17a-17b are sectional views of a distal portion of a clot retrieval catheter of the invention.

FIG. 17a is a cross sectional view of another embodiment of the invention. This figure shows the distal end of a clot retrieval catheter 1100 in its introduced configuration prior to expansion of the expansile element 1107. The catheter is constructed with an expansile element or balloon 1107 mounted on the body section 1109 of the catheter. The balloon is bonded at the proximal and distal ends at 1105 and 1104 respectively and communicates with an inflation lumen (not shown) to facilitate expansion. A strip of material 1108 is mounted over the balloon and joined proximally 1106 to the catheter body 1109. The distal end of the material strip 1108 is bonded to the atraumatic distal catheter tip 1102. In this configuration the distal end of the strip 1108 is inverted 1103 prior to joining to the catheter tip 1102. A number of material strips 1108 are positioned radially around the balloon 1107.

Figure 17B:
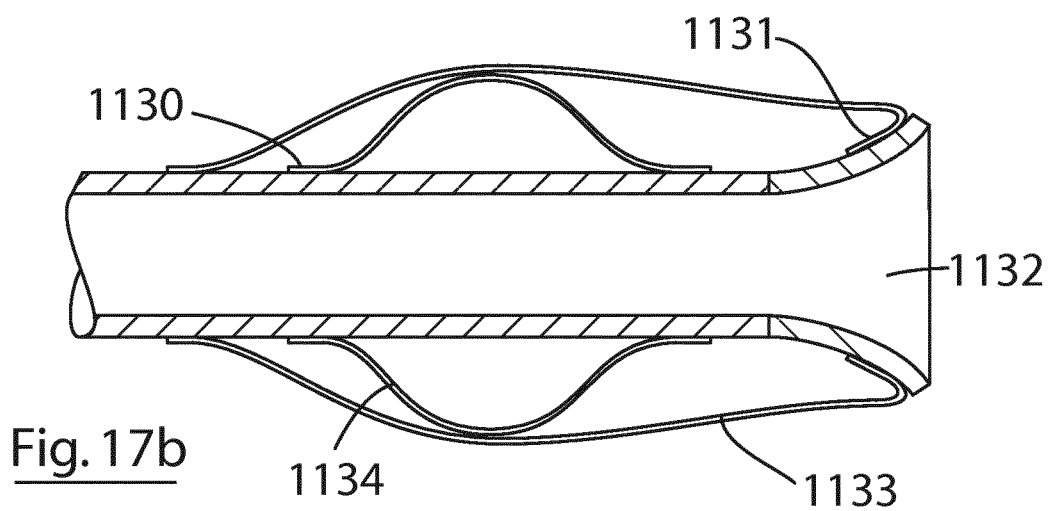

FIG. 17b shows the device 1100 in its deployed or expanded configuration. Fluid has been injected into the balloon 1134 to expand it and occlude the vessel producing flow arrest to improve the efficacy of clot retrieval. In this embodiment, the material strips 1133 are produced from a low elastic compliance polymer with a thin wall such as PET. These material strips 1133 are put under tension when the balloon 1134 expands and this tension causes the atraumatic tip of the catheter 1132 to deform, expanding the distal edge and producing a funnel shape 1132. By inverting the end 1131 of the strip 1133 prior to joining to the catheter tip, it ensures the tension applied to the tip is at the distal end, producing a larger diameter funnel shape.

Figure 17C:
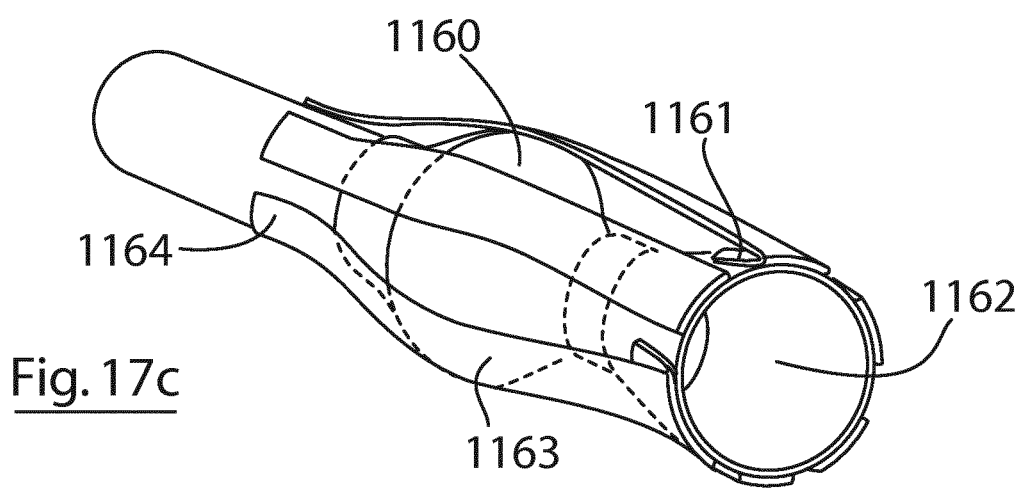
FIG. 17c is an isometric view of a distal end of the catheter of FIGS. 17a and 17b.

FIG. 17c is an isometric type view of a device similar to that shown in FIG. 17b. In this case material strips 1163 are positioned radially around the balloon 1160 and are joined to the catheter proximal of the balloon at 1164. The distal ends of the strips 1163 are inverted 1161 and bonded to the catheter tip 1162. Expansion of balloon 1160 pushes out the material strips 1163 causing a tension to be applied to the catheter tip 1162 forming a funnel shape.

FIG. 18a is a sectional schematic of another embodiment of the invention. The distal end 1200 of the catheter is constructed of a distal balloon 1201 mounted on a catheter shaft 1203. As before, when balloon 1201 is expanded it provides flow arrest capability in the vessel by occluding flow. In addition, expansion of the balloon applies tension to the catheter tip 1202 causing it to form a funnel shape improving lead-in for the clot, reducing clot shear and improving the efficacy of aspiration and clot retrieval with a stentriever.

FIG. 18b is a section view A-A from FIG. 18a and illustrates a composite balloon construction which consists of semi-rigid ribs 1222 interspersed with sections of elastic expansile material 1221. When fluid is introduced into the balloon through the inflation lumen (not shown), pressure increases and the soft segments 1221 expand in diameter creating flow occlusion in the vessel. The ribs 1222 which can have a different durometer to the expansile segments 1221 are more efficient at transferring tension to the distal tip and enhance the ability of the balloon to expand the tip to form a funnel shape. The ribs 1222 may be co-extruded with the balloon material or may be formed by integrating a wire or other material into the balloon extrusion. The ribs may run parallel to the axis of the catheter or may be formed in a spiral configuration to improve the flow arrest capabilities of the balloon.

FIG. 18*c* shows section A-A in the non-expanded configuration with the ribs 1242 and expansile segments 1241 concentric during introduction of the catheter to the target location.

FIG. 18*d* shows an alternative balloon section view in the non-expanded configuration. In this embodiment the balloon 1260 is formed from a single profiled extrusion with varying wall thickness around the circumference. The areas with reduced wall thickness 1261 expand under pressure creating flow arrest in the vessel while the segments with increased wall thickness 1262 act as ribs applying tension to the atraumatic catheter tip, causing it to expand.

Figure 19A:
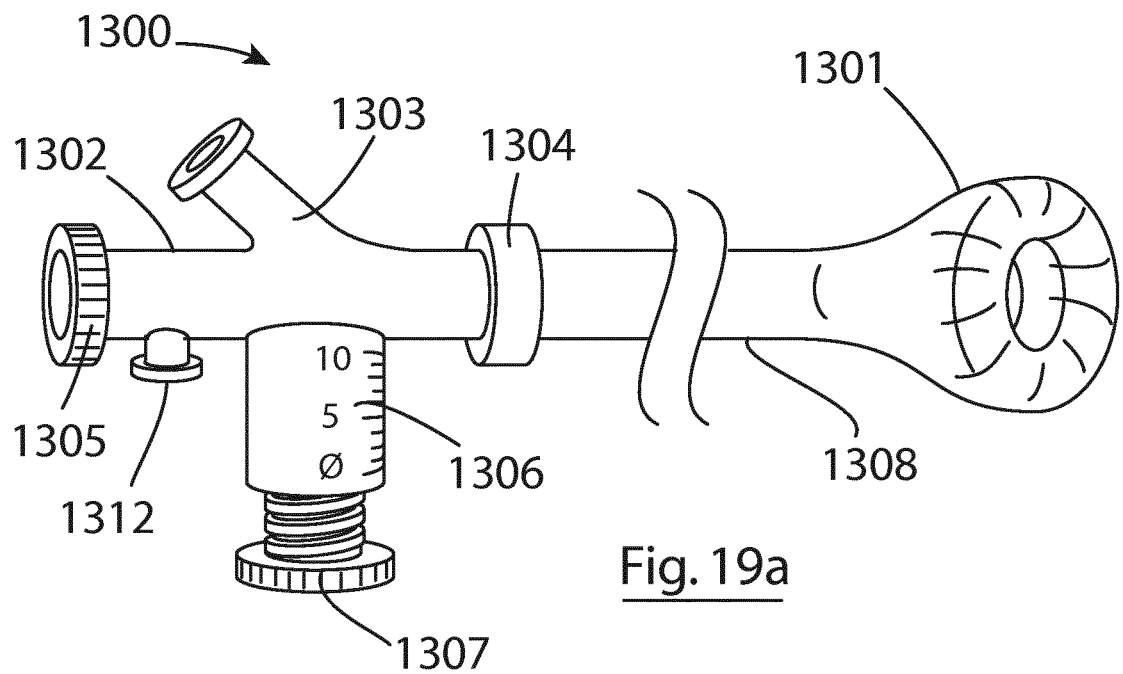
FIGS. 19a-19b are views of the proximal hub of a clot retrieval catheter of the invention.

FIG. 19*a* shows a stylized view of a handle or proximal region of one embodiment of a clot retrieval catheter 1300 of this invention in which inflation and deflation of the balloon 1301 can be performed without any need to prepare or flush the inflation area in advance. This is made possible by a sealed system in which the inflation lumen and inflation regions are evacuated of all air and then filled with a sterile radiopaque solution. Thus the operator need simply turn the threaded knob or actuator 1307 to inflate the balloon 1301 to the desired diameter. The catheter 1300 comprises an elongate shaft 1308 with an inflatable balloon 1301 at its distal end and a proximal hub assembly 1302 at its proximal end. The shaft and balloon may be configured as per any of those previously disclosed herein. The proximal hub assembly comprises an inflation controller 1306, a side port 1303 (optional), a preparation port 1311 and a proximal connector 1305. Proximal connector 1305 may be a rotating hemostasis valve or may be simply a luer or connector to which a valve or other luer, connector or fitting may be attached, and/or through which other catheters or devices may be advanced or retracted. The sterile radiopaque solution held within the chamber 1314, which is within the inflation controller 1306, may comprise contrast media such as an iodine solution.

Figure 19B:
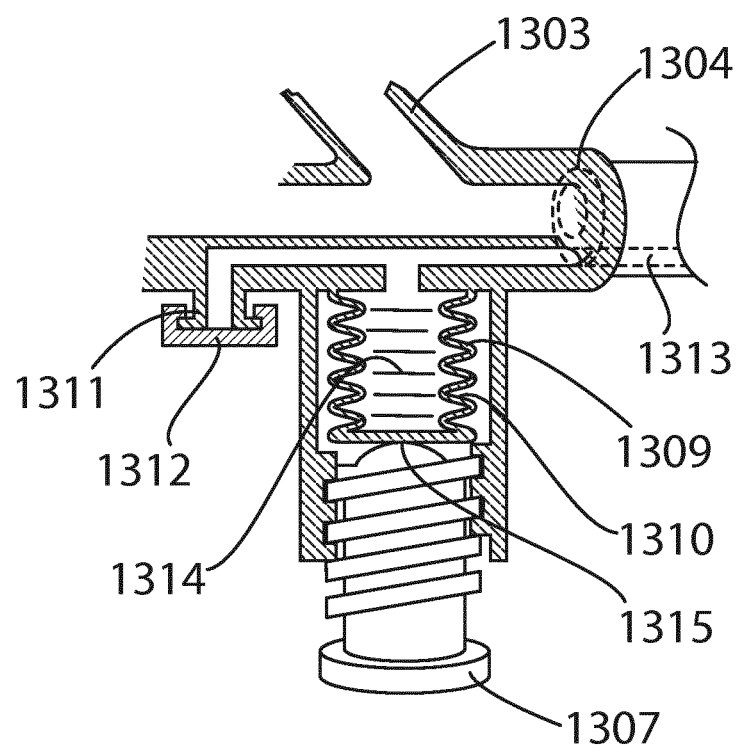

FIG. 19*b* shows a sectional view through a portion of the proximal hub assembly 1302 of the catheter 1300 of FIG. 19*a*. Clockwise rotation of threaded knob 1307 causes the end 1315 of the knob 1307 to compress the corrugated member 1310. This in turn reduces the volume of the chamber 1314 within the corrugated member 1310, forcing fluid (which may be sterile contrast media) out of the chamber and into the inflation lumen 1313 which runs from the inflation controller through the elongate shaft 1308 to the distal inflatable balloon 1301. This in turn causes the balloon to inflate, and the degree of inflation can be controlled by controlling the depth to which the knob is screwed into the inflation controller. A transparent inflation controller body 1306 may be used, through which a dark/opaque knob will be visible, allowing the operator to align the end of the knob 1315 with an appropriate marking on the controller body. Counter-clockwise rotation of the knob 1307 allows corrugated chamber 1310 to expand, and this expansion may be assisted by means of a coil spring 1309. This expansion pulls fluid back through the inflation port from the balloon, deflating the balloon.

Preparation port 1311 and sealing cap 1312 are used to evacuate, fill and seal the unit prior to use. In a preferred embodiment these steps are performed by the manufacturer and the unit is provided to the customer ready for use.

In an alternative embodiment these steps of evacuating, prepping and sealing may be done by a second operator (such as a cath lab nurse or technician or fellow) prior to use of the device by a first operator.

Figure 20A:
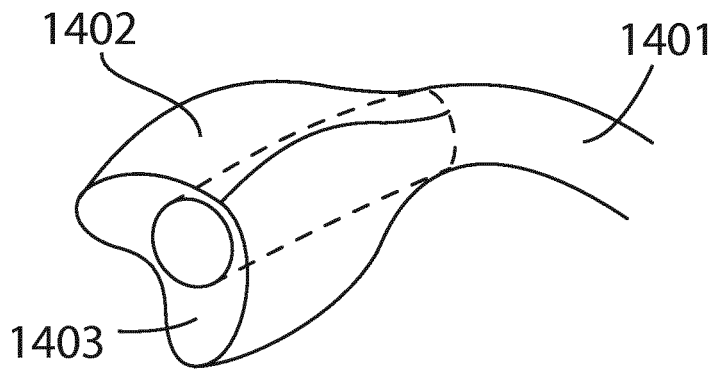
FIGS. 20a and 20b are isometric views of the distal end of clot retrieval catheters of the invention.

FIG. 20*a* shows the distal end of a different embodiment of the invention where the balloon 1402 is mounted on the catheter shaft 1401. The balloon 1402 is shown in the expanded configuration and the distal tip 1403 forms a non-uniform shape. The tip 1403 still provides a lead-in for clot during retrieval improving efficacy and reducing clot shear. The distal tip shape may be symmetrical and align with bending elements of the catheter shaft.

Figure 20B:
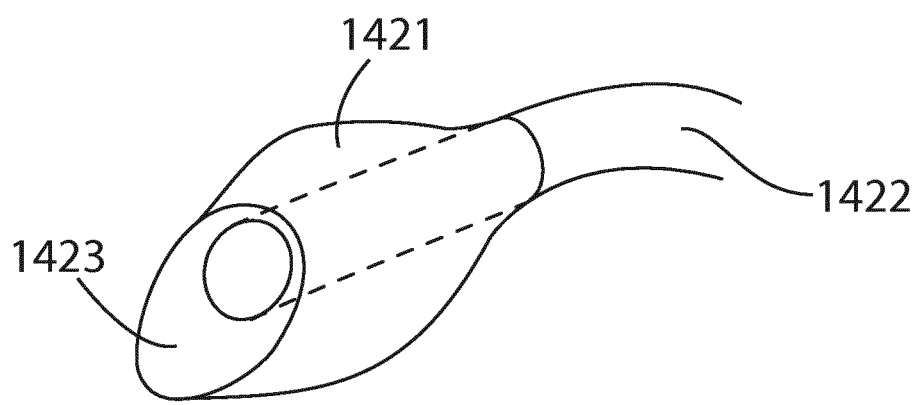

FIG. 20*b* shows an alternative embodiment where the atraumatic distal tip 1423 forms an eccentric shape during introduction and may also expand to form an eccentric lead-in or funnel for the clot.

Figure 20C:
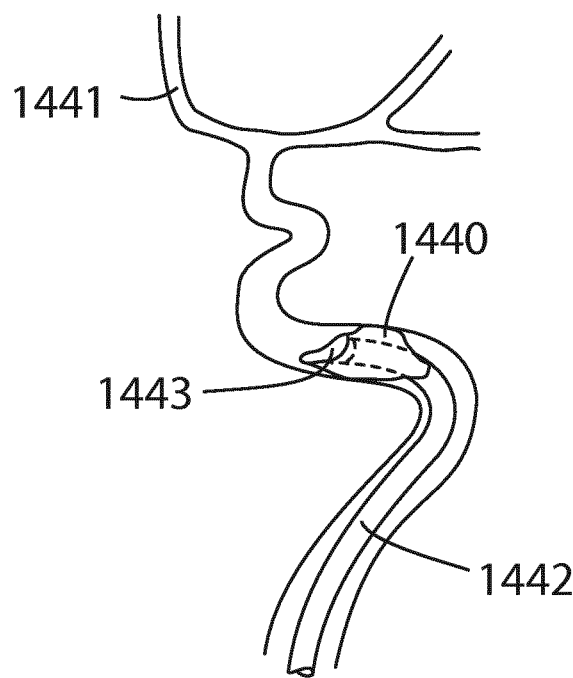
FIG. 20c is a simplified view of a clot retrieval catheter of the invention, in use.

FIG. 20*c* illustrates how a catheter similar to the catheter of FIG. 20*b* may be positioned in the neurovasculature 1441 so that the balloon 1440 produces flow arrest and the eccentric tip 1443 provides a lead-in for clot retrieval. In one embodiment of such a system the catheter shaft 1442 is biased with a curved shape in the unconstrained condition in order to assist in orienting the eccentric balloon tip appropriately to the vasculature. In one embodiment this curve comprises a curve immediately proximal of the balloon 1440 as shown. In another embodiment the curve comprises a more proximal curve, which is designed to be positioned within the aortic arch of the patient. In yet another embodiment the catheter comprises both such curves. In yet another embodiment the catheter comprises a plurality of curves. In yet another embodiment the catheter comprises a steerable element by which a curve can be selectively applied to the catheter during or after its advancement through the vasculature to the target site.

It will be apparent from the foregoing description that while particular embodiments of the present invention have been illustrated and described, various modifications can be made without departing from the spirit and scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

The invention claimed is:

1. A clot capture catheter comprising an elongate tubular shaft having a proximal end, a distal end and an inflatable expansile member at the distal end, the inflatable expansile member being inflatable from a collapsed delivery configuration to an expanded configuration, wherein the inflatable expansile member comprises a balloon;

wherein, in the expanded configuration, the inflatable expansile member extends to at least a distalmost tip of the elongate tubular shaft and extends radially outwardly from the elongate tubular shaft at the distalmost tip of the elongate tubular shaft to define a mouth;

wherein expansion of the balloon applies tension to the distalmost tip of the elongate tubular shaft, thereby causing a distal portion of the elongate tubular shaft to form a funnel shape; and wherein the distal portion of the elongate tubular shaft comprises a distal section and a proximal section of differing stiffnesses and defining a hinge therebetween, the distal section having a lower bending stiffness than the proximal section, and the hinge being circumscribed by the balloon.

2. The catheter of claim 1, wherein the balloon is integral to the distalmost tip of the elongate tubular shaft, wherein the balloon is formed from a polymeric tube which is inverted so that a distal junction between the balloon and the elongate tubular shaft is located within the balloon.

3. The catheter of claim 1, wherein the balloon comprises a proximal region, a distal region and a median region between the proximal and distal regions and wherein, in the expanded configuration, the distal region expands to a greater extent than the proximal region.

4. The catheter of claim 3, wherein at least one region has a different wall thickness than at least one other region.

5. The catheter of claim 3, wherein the inflatable expansile member comprises:
- a proximal neck and a distal neck, the proximal neck having a first thickness, and being connected to the elongate tubular shaft proximal of the distal end of the elongate tubular shaft,
- a proximal portion of the balloon comprising a second thickness,
- a distal portion of the balloon comprising a third thickness, and
- the distal neck, which is inverted and joined to the distal end of the elongate tubular shaft, comprising a fourth thickness.

6. The catheter of claim 5, further comprising a band between the proximal and distal regions of the balloon, the band having a greater wall thickness than a wall thickness of the proximal and/or distal regions of the balloon to create a relatively non-expansile region such that the balloon preferentially inflates proximal and distal of the band to provide a funnel shape profile.

7. The catheter of claim 6, wherein at least one region of the proximal or distal regions of the balloon is reinforced to limit the expansion of that region.

8. The catheter of claim 7, wherein the proximal region comprises a reinforcement, wherein the reinforcement comprises ribs, wherein the ribs extend axially and/or radially along at least a portion of the proximal region.

9. The catheter of claim 1, wherein the inflatable expansile member extends beyond the distalmost tip of the elongate tubular shaft for a distance of from 0.5 mm to 3.5 mm;

wherein the elongate tubular shaft comprises a main inner lumen, and an inflation lumen for inflating the inflatable expansile member.

10. The catheter of claim 9, wherein the inflation lumen and the main inner lumen are concentric.

11. The catheter of claim 9, wherein a distal portion of the elongate tubular shaft comprises a first amorphous elastomeric polymer and the inflatable expansile member comprises a second amorphous elastomeric polymer which is different than the first amorphous elastomeric polymer.

12. The catheter of claim 1, further comprising a radiopaque expansile marker band at or adjacent to the inflatable expansile member, wherein the radiopaque expansile marker band is located beneath the inflatable expansile member, wherein the radiopaque expansile marker band is of generally tubular shape having axially extending slots which are configured to facilitate expansion of the radiopaque expansile marker band.

13. The catheter of claim 1, wherein a strip of material is mounted over the inflatable expansile member and joined proximally to the elongate tubular shaft and a distal end of the material strip is bonded to an atraumatic distalmost tip of the elongate tubular shaft.

14. The catheter of claim 13, wherein a plurality of material strips are positioned radially around the balloon.

* * * * *